(12) United States Patent
Williams et al.

(10) Patent No.: US 11,298,126 B2
(45) Date of Patent: Apr. 12, 2022

(54) SHIPPING WEDGE FOR END EFFECTOR INSTALLATION ONTO SURGICAL DEVICES

(71) Applicant: Covidien LP, Mansfield, MA (US)

(72) Inventors: Justin Williams, Southbury, CT (US); David M. Farascioni, Bethel, CT (US); Jin Yong, Watertown, CT (US); John W. Beardsley, Wallingford, CT (US); Joseph Leveillee, Cheshire, CT (US); Stanislaw Kostrzewski, Newtown, CT (US); Michael J. Kolb, Southington, CT (US); Kevin S. Sniffin, Roxbury, CT (US); Mark A. Russo, Plantsville, CT (US); Brian S. Laird, Granby, CT (US)

(73) Assignee: COVIDIEN LP, Mansfield, MA (US)

( * ) Notice: Subject to any disclaimer, the term of this patent is extended or adjusted under 35 U.S.C. 154(b) by 316 days.

(21) Appl. No.: 16/279,180

(22) Filed: Feb. 19, 2019

(65) Prior Publication Data
US 2019/0336126 A1 Nov. 7, 2019

Related U.S. Application Data

(60) Provisional application No. 62/665,548, filed on May 2, 2018.

(51) Int. Cl.
*A61B 50/30* (2016.01)
*A61B 17/068* (2006.01)
(Continued)

(52) U.S. Cl.
CPC .......... *A61B 17/068* (2013.01); *A61B 17/064* (2013.01); *A61B 50/30* (2016.02);
(Continued)

(58) Field of Classification Search
CPC . A61B 2090/038; A61B 50/30; A61B 17/068; A61B 17/064; A61B 17/00234; A61B 17/0688; A61B 2017/0688
(Continued)

(56) References Cited

U.S. PATENT DOCUMENTS

| | | |
|---|---|---|
| 3,596,528 A | 8/1971 | Dittrich et al. |
| 3,866,510 A | 2/1975 | Eibes et al. |

(Continued)

FOREIGN PATENT DOCUMENTS

| | | |
|---|---|---|
| EP | 0374088 A1 | 6/1990 |
| JP | 09149906 | 6/1997 |

OTHER PUBLICATIONS

Extended European Search Report corresponding to EP 14 15 8946.5, completed Jun. 20, 2014 and dated Jul. 8, 2014; (9 pp).

(Continued)

*Primary Examiner* — Steven A. Reynolds

(57) ABSTRACT

Shipping wedges for installing end effectors onto an endoscopic assembly of a surgical tack applier are provided. In aspects, a shipping wedge includes an elongate body extending along a longitudinal axis and defining a channel therethrough, and an arm disposed within a slot defined in a side wall of the elongate body. The arm includes a first end coupled to the side wall and a second end that is movable laterally with respect to the side wall. In aspects, a shipping wedge includes an elongate body extending along a longitudinal axis and defining a channel therethrough. A proximal portion of the elongate body includes a first arm extending proximally from a distal portion of the elongate body and a locking tab extending laterally into the channel of the elongate body.

20 Claims, 22 Drawing Sheets

(51) Int. Cl.
*A61B 17/064* (2006.01)
*A61B 90/00* (2016.01)
*A61B 17/00* (2006.01)

(52) U.S. Cl.
CPC . *A61B 17/00234* (2013.01); *A61B 2017/0688* (2013.01); *A61B 2090/038* (2016.02)

(58) Field of Classification Search
USPC .................................................. 206/438, 363
See application file for complete search history.

(56) References Cited

U.S. PATENT DOCUMENTS

| | | |
|---|---|---|
| 4,350,491 A | 9/1982 | Steuer |
| 4,730,726 A | 3/1988 | Holzwarth |
| 4,884,572 A | 12/1989 | Bays et al. |
| 5,085,661 A | 2/1992 | Moss |
| 5,144,942 A | 9/1992 | Decarie et al. |
| 5,156,267 A | 10/1992 | Yates, Jr. et al. |
| 5,171,247 A | 12/1992 | Hughett et al. |
| 5,171,249 A | 12/1992 | Stefanchik et al. |
| 5,176,306 A | 1/1993 | Heimerl et al. |
| 5,207,697 A | 5/1993 | Carusillo et al. |
| 5,228,256 A | 7/1993 | Dreveny |
| 5,236,563 A | 8/1993 | Loh |
| 5,246,441 A | 9/1993 | Ross et al. |
| 5,246,450 A | 9/1993 | Thornton et al. |
| 5,312,023 A | 5/1994 | Green et al. |
| 5,330,487 A | 7/1994 | Thornton et al. |
| 5,344,061 A | 9/1994 | Crainich |
| 5,353,929 A | 10/1994 | Foster |
| 5,356,064 A | 10/1994 | Green et al. |
| 5,381,896 A | 1/1995 | Simons |
| 5,382,254 A | 1/1995 | McGarry et al. |
| 5,398,861 A | 3/1995 | Green |
| 5,403,327 A | 4/1995 | Thornton et al. |
| 5,407,070 A | 4/1995 | Bascos et al. |
| 5,433,721 A | 7/1995 | Hooven et al. |
| 5,439,468 A | 8/1995 | Schulze et al. |
| 5,466,243 A | 11/1995 | Schmieding et al. |
| 5,467,911 A | 11/1995 | Tsuruta et al. |
| 5,474,566 A | 12/1995 | Alesi et al. |
| 5,474,567 A | 12/1995 | Stefanchik et al. |
| 5,522,844 A | 6/1996 | Johnson |
| 5,527,319 A | 6/1996 | Green et al. |
| 5,553,765 A | 9/1996 | Knodel et al. |
| 5,562,685 A | 10/1996 | Mollenauer et al. |
| 5,564,615 A | 10/1996 | Bishop et al. |
| 5,582,615 A | 12/1996 | Foshee et al. |
| 5,582,616 A | 12/1996 | Bolduc et al. |
| 5,584,425 A | 12/1996 | Savage et al. |
| 5,588,581 A | 12/1996 | Conlon et al. |
| 5,601,571 A | 2/1997 | Moss |
| 5,601,573 A | 2/1997 | Fogelberg et al. |
| 5,607,436 A | 3/1997 | Pratt et al. |
| 5,626,613 A | 5/1997 | Schmieding |
| 5,628,752 A | 5/1997 | Asnis et al. |
| 5,649,931 A | 7/1997 | Bryant et al. |
| 5,662,662 A | 9/1997 | Bishop et al. |
| 5,681,330 A | 10/1997 | Hughett et al. |
| 5,683,401 A | 11/1997 | Schmieding et al. |
| 5,685,474 A | 11/1997 | Seeber |
| 5,697,935 A | 12/1997 | Moran et al. |
| 5,704,534 A | 1/1998 | Huitema et al. |
| 5,709,692 A | 1/1998 | Mollenauer et al. |
| 5,728,116 A | 3/1998 | Rosenman |
| 5,730,744 A | 3/1998 | Justin et al. |
| 5,732,806 A | 3/1998 | Foshee et al. |
| 5,735,854 A | 4/1998 | Caron et al. |
| 5,741,268 A | 4/1998 | Schutz |
| 5,762,255 A | 6/1998 | Chrisman et al. |
| 5,782,844 A | 7/1998 | Yoon et al. |
| 5,792,165 A | 8/1998 | Klieman et al. |
| 5,810,882 A | 9/1998 | Bolduc et al. |
| 5,824,008 A | 10/1998 | Bolduc et al. |
| 5,830,221 A | 11/1998 | Stein et al. |
| 5,843,087 A | 12/1998 | Jensen et al. |
| 5,897,564 A | 4/1999 | Schulze et al. |
| 5,904,693 A | 5/1999 | Dicesare et al. |
| 5,910,105 A | 6/1999 | Swain et al. |
| 5,911,722 A | 6/1999 | Adler et al. |
| 5,928,244 A | 7/1999 | Tovey et al. |
| 5,928,252 A | 7/1999 | Steadman et al. |
| 5,931,844 A | 8/1999 | Thompson et al. |
| 5,941,439 A | 8/1999 | Kammerer et al. |
| 5,954,259 A | 9/1999 | Viola et al. |
| 5,961,524 A | 10/1999 | Crombie |
| 5,964,772 A | 10/1999 | Bolduc et al. |
| 5,976,160 A | 11/1999 | Crainich |
| 5,997,552 A | 12/1999 | Person et al. |
| 6,010,513 A | 1/2000 | Tormala et al. |
| 6,013,991 A | 1/2000 | Philipp |
| 6,039,753 A | 3/2000 | Meislin |
| 6,074,395 A | 6/2000 | Trott et al. |
| 6,099,537 A | 8/2000 | Sugai et al. |
| 6,126,670 A | 10/2000 | Walker et al. |
| 6,132,435 A | 10/2000 | Young |
| 6,146,387 A | 11/2000 | Trott et al. |
| 6,183,479 B1 | 2/2001 | Tormala et al. |
| 6,228,098 B1 | 5/2001 | Kayan et al. |
| 6,235,058 B1 | 5/2001 | Huene |
| 6,241,736 B1 | 6/2001 | Sater et al. |
| 6,261,302 B1 | 7/2001 | Voegele et al. |
| 6,296,656 B1 | 10/2001 | Bolduc et al. |
| 6,330,964 B1 | 12/2001 | Kayan et al. |
| 6,387,113 B1 | 5/2002 | Hawkins et al. |
| 6,402,757 B1 | 6/2002 | Moore, III et al. |
| 6,402,780 B2 | 6/2002 | Williamson, IV et al. |
| 6,425,900 B1 | 7/2002 | Knodel et al. |
| 6,439,446 B1 | 8/2002 | Perry et al. |
| 6,440,136 B1 | 8/2002 | Gambale et al. |
| 6,450,391 B1 | 9/2002 | Kayan et al. |
| 6,457,625 B1 | 10/2002 | Tormala et al. |
| 6,551,333 B2 | 4/2003 | Kuhns et al. |
| 6,562,051 B1 | 5/2003 | Bolduc et al. |
| 6,572,626 B1 | 6/2003 | Knodel et al. |
| 6,589,249 B2 | 7/2003 | Sater et al. |
| 6,592,593 B1 | 7/2003 | Parodi et al. |
| 6,626,916 B1 | 9/2003 | Yeung et al. |
| 6,632,228 B2 | 10/2003 | Fortier et al. |
| 6,652,538 B2 | 11/2003 | Kayan et al. |
| 6,663,656 B2 | 12/2003 | Schmieding et al. |
| 6,666,854 B1 | 12/2003 | Lange |
| 6,695,867 B2 | 2/2004 | Ginn et al. |
| 6,733,506 B1 | 5/2004 | McDevitt et al. |
| 6,743,240 B2 | 6/2004 | Smith et al. |
| 6,749,621 B2 | 6/2004 | Pantages et al. |
| 6,755,836 B1 | 6/2004 | Lewis |
| 6,773,438 B1 | 8/2004 | Knodel et al. |
| 6,800,081 B2 | 10/2004 | Parodi |
| 6,811,552 B2 | 11/2004 | Weil, Sr. et al. |
| 6,824,548 B2 | 11/2004 | Smith et al. |
| 6,837,893 B2 | 1/2005 | Miller |
| 6,840,943 B2 | 1/2005 | Kennefick et al. |
| 6,843,794 B2 | 1/2005 | Sixto, Jr. et al. |
| 6,869,435 B2 | 3/2005 | Blake, III |
| 6,884,248 B2 | 4/2005 | Bolduc et al. |
| 6,887,244 B1 | 5/2005 | Walker et al. |
| 6,893,446 B2 | 5/2005 | Sater et al. |
| 6,905,057 B2 | 6/2005 | Swayze et al. |
| 6,929,661 B2 | 8/2005 | Bolduc et al. |
| 6,942,674 B2 | 9/2005 | Belef et al. |
| 6,945,979 B2 | 9/2005 | Kortenbach et al. |
| 6,960,217 B2 | 11/2005 | Bolduc |
| 6,966,919 B2 | 11/2005 | Sixto, Jr. et al. |
| 6,988,650 B2 | 1/2006 | Schwemberger et al. |
| 7,000,819 B2 | 2/2006 | Swayze et al. |
| 7,070,601 B2 | 7/2006 | Culbert et al. |
| 7,122,028 B2 | 10/2006 | Looper et al. |
| 7,128,754 B2 | 10/2006 | Bolduc |
| 7,147,657 B2 | 12/2006 | Chiang et al. |
| 7,204,847 B1 | 4/2007 | Gambale |
| 7,261,716 B2 | 8/2007 | Strobel et al. |
| 7,357,287 B2 | 4/2008 | Shelton, IV et al. |

(56) References Cited

U.S. PATENT DOCUMENTS

| | | |
|---|---|---|
| 7,380,696 B2 | 6/2008 | Shelton, IV et al. |
| 7,404,508 B2 | 7/2008 | Smith et al. |
| 7,410,086 B2 | 8/2008 | Ortiz et al. |
| 7,434,717 B2 | 10/2008 | Shelton, IV et al. |
| 7,461,574 B2 | 12/2008 | Lewis et al. |
| 7,491,232 B2 | 2/2009 | Bolduc et al. |
| 7,544,198 B2 | 6/2009 | Parodi |
| 7,591,842 B2 | 9/2009 | Parodi |
| 7,611,521 B2 | 11/2009 | Lubbers et al. |
| 7,637,905 B2 | 12/2009 | Saadat et al. |
| 7,637,932 B2 | 12/2009 | Bolduc et al. |
| 7,670,362 B2 | 3/2010 | Zergiebel |
| 7,740,159 B2 | 6/2010 | Shelton, IV et al. |
| 7,758,612 B2 | 7/2010 | Shipp |
| 7,811,312 B2 | 10/2010 | Stevens et al. |
| 7,819,884 B2 | 10/2010 | Lee et al. |
| 7,823,267 B2 | 11/2010 | Bolduc |
| 7,828,838 B2 | 11/2010 | Bolduc et al. |
| 7,862,573 B2 | 1/2011 | Darois et al. |
| 7,867,252 B2 | 1/2011 | Criscuolo et al. |
| 7,905,890 B2 | 3/2011 | Whitfield et al. |
| 7,913,892 B2 | 3/2011 | Cole et al. |
| 7,922,061 B2 | 4/2011 | Shelton, IV et al. |
| 7,922,063 B2 | 4/2011 | Zemlok et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi et al. |
| 8,006,365 B2 | 8/2011 | Levin et al. |
| 8,034,076 B2 | 10/2011 | Criscuolo et al. |
| 8,062,306 B2 | 11/2011 | Nobis et al. |
| 8,075,570 B2 | 12/2011 | Bolduc et al. |
| 8,083,752 B2 | 12/2011 | Bolduc |
| 8,087,142 B2 | 1/2012 | Levin et al. |
| 8,092,519 B2 | 1/2012 | Bolduc |
| 8,114,099 B2 | 2/2012 | Shipp |
| 8,114,101 B2 | 2/2012 | Criscuolo et al. |
| 8,152,820 B2 | 4/2012 | Mohamed et al. |
| 8,181,840 B2 | 5/2012 | Milliman |
| 8,216,254 B2 | 7/2012 | McLean et al. |
| 8,216,272 B2 | 7/2012 | Shipp |
| 8,225,979 B2* | 7/2012 | Farascioni ....... A61B 17/07207 227/175.2 |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,333,776 B2 | 12/2012 | Cheng et al. |
| 8,343,176 B2 | 1/2013 | Criscuolo et al. |
| 8,343,184 B2 | 1/2013 | Blier |
| 8,377,044 B2 | 2/2013 | Coe et al. |
| 8,382,773 B2 | 2/2013 | Whitfield et al. |
| 8,382,778 B2 | 2/2013 | Criscuolo et al. |
| 8,414,627 B2 | 4/2013 | Corradi et al. |
| 8,424,740 B2 | 4/2013 | Shelton, IV et al. |
| 8,465,520 B2 | 6/2013 | Blier |
| 8,474,679 B2 | 7/2013 | Felix |
| 8,579,919 B2 | 11/2013 | Bolduc et al. |
| 8,579,920 B2 | 11/2013 | Nering et al. |
| 8,597,311 B2 | 12/2013 | Criscuolo et al. |
| 8,603,135 B2 | 12/2013 | Mueller |
| 8,672,209 B2 | 3/2014 | Crainich |
| 8,684,247 B2 | 4/2014 | Scirica et al. |
| 8,685,044 B2 | 4/2014 | Bolduc et al. |
| 8,690,889 B2 | 4/2014 | Colesanti et al. |
| 8,690,897 B2 | 4/2014 | Bolduc |
| 8,728,098 B2 | 5/2014 | Daniel et al. |
| 8,728,099 B2 | 5/2014 | Cohn et al. |
| 8,728,102 B2 | 5/2014 | Criscuolo et al. |
| 8,728,120 B2 | 5/2014 | Blier |
| 8,777,969 B2 | 7/2014 | Kayan |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,894,669 B2 | 11/2014 | Nering et al. |
| 8,920,439 B2 | 12/2014 | Cardinale et al. |
| 8,926,637 B2 | 1/2015 | Zergiebel |
| 9,017,345 B2 | 4/2015 | Taylor et al. |
| 9,023,065 B2 | 5/2015 | Bolduc et al. |
| 9,028,495 B2 | 5/2015 | Mueller et al. |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 | 5/2016 | Shipp |
| 9,345,462 B2 | 5/2016 | Weitzner et al. |
| 9,351,728 B2 | 5/2016 | Sniffin et al. |
| 9,351,733 B2 | 5/2016 | Fischvogt |
| 9,358,004 B2 | 6/2016 | Sniffin et al. |
| 9,358,010 B2 | 6/2016 | Wenchell et al. |
| 9,364,231 B2 | 6/2016 | Wenchell |
| 9,364,274 B2 | 6/2016 | Zergiebel |
| 9,386,983 B2 | 7/2016 | Swensgard et al. |
| 9,402,623 B2 | 8/2016 | Kayan |
| 9,445,814 B2 | 9/2016 | Ranucci et al. |
| 9,486,218 B2 | 11/2016 | Criscuolo et al. |
| 9,526,498 B2 | 12/2016 | Reed |
| 9,615,830 B2 | 4/2017 | Ranucci et al. |
| 9,655,621 B2 | 5/2017 | Abuzaina et al. |
| 9,662,106 B2 | 5/2017 | Corradi et al. |
| 9,668,730 B2 | 6/2017 | Sniffin et al. |
| 9,783,329 B2* | 10/2017 | Sniffin ..................... B65B 5/10 |
| 9,788,833 B2 | 10/2017 | Zergiebel et al. |
| 9,801,633 B2 | 10/2017 | Sholev et al. |
| 9,867,620 B2 | 1/2018 | Fischvogt et al. |
| 9,987,010 B2 | 6/2018 | Zergiebel |
| 10,070,860 B2 | 9/2018 | Zergiebel |
| 2003/0009441 A1 | 1/2003 | Holsten et al. |
| 2003/0114839 A1 | 6/2003 | Looper et al. |
| 2004/0092937 A1 | 5/2004 | Criscuolo et al. |
| 2005/0222665 A1 | 10/2005 | Aranyi |
| 2006/0129152 A1 | 6/2006 | Shipp |
| 2006/0129154 A1 | 6/2006 | Shipp |
| 2007/0038220 A1 | 2/2007 | Shipp |
| 2007/0088390 A1 | 4/2007 | Paz et al. |
| 2007/0106317 A1 | 5/2007 | Shelton et al. |
| 2007/0162030 A1 | 7/2007 | Aranyi et al. |
| 2008/0086154 A1 | 4/2008 | Taylor et al. |
| 2008/0097523 A1 | 4/2008 | Bolduc et al. |
| 2008/0312687 A1 | 12/2008 | Blier |
| 2009/0112234 A1 | 4/2009 | Crainich et al. |
| 2009/0118776 A1 | 5/2009 | Kelsch et al. |
| 2009/0188965 A1 | 7/2009 | Levin et al. |
| 2010/0137886 A1 | 6/2010 | Zergiebel et al. |
| 2010/0270354 A1 | 10/2010 | Rimer et al. |
| 2011/0022065 A1 | 1/2011 | Shipp |
| 2011/0101066 A1 | 5/2011 | Farascioni et al. |
| 2011/0295282 A1 | 12/2011 | Glick et al. |
| 2012/0059397 A1 | 3/2012 | Criscuolo et al. |
| 2012/0109157 A1 | 5/2012 | Criscuolo et al. |
| 2012/0234894 A1* | 9/2012 | Kostrzewski .... A61B 17/07207 227/175.2 |
| 2014/0005678 A1 | 1/2014 | Shelton, IV et al. |
| 2014/0014707 A1 | 1/2014 | Onukuri et al. |
| 2014/0200587 A1 | 7/2014 | Pompee et al. |
| 2014/0243855 A1 | 8/2014 | Sholev et al. |
| 2014/0252065 A1 | 9/2014 | Hessler et al. |
| 2015/0032130 A1 | 1/2015 | Russo |
| 2015/0129632 A1* | 5/2015 | Kostrzewski ...... A61B 17/0686 227/175.2 |
| 2015/0133970 A1 | 5/2015 | Ranucci et al. |
| 2015/0190133 A1 | 7/2015 | Penna et al. |
| 2015/0327859 A1 | 11/2015 | Bolduc |
| 2016/0000428 A1 | 1/2016 | Scirica et al. |
| 2016/0007991 A1 | 1/2016 | Bolduc |
| 2016/0007996 A1 | 1/2016 | Bolduc |
| 2016/0074034 A1 | 3/2016 | Shipp |
| 2016/0166255 A1 | 6/2016 | Fischvogt |
| 2016/0192927 A1 | 7/2016 | Kostrzewski |
| 2016/0249912 A1 | 9/2016 | Fischvogt |
| 2016/0270835 A1 | 9/2016 | Reed |
| 2016/0278766 A1 | 9/2016 | Wenchell et al. |
| 2016/0338694 A1 | 11/2016 | Kayan |

(56) References Cited

U.S. PATENT DOCUMENTS

2016/0345967 A1 12/2016 Sniffin et al.
2017/0231631 A1 8/2017 Abuzaina et al.
2017/0265859 A1 9/2017 Sniffin et al.
2018/0042591 A1 2/2018 Russo et al.
2018/0116670 A1 5/2018 Fischvogt et al.

OTHER PUBLICATIONS

Extended European Search Report corresponding to EP 14 17 8107.0, completed Nov. 24, 2014 and dated Dec. 3, 2014; (5 pp).
Extended European Search Report corresponding to EP 14 17 4656.0, completed Jan. 16, 2015 and dated Jan. 26, 2015; (7 pp).
Extended European Search Report corresponding to EP 14 18 4907.5, completed Jan. 12, 2015 and dated Jan. 27, 2015; (9 pp).
European Search Report corresponding to EP 14 18 1900.3, completed Mar. 31, 2015 and dated Apr. 9, 2015; 7pp.
Extended European Search Report corresponding to EP 14 19 7885.8 dated Apr. 30, 2015.
Extended European Search Report corresponding to EP No. 11 25 0549.0, completed Sep. 9, 2013 and dated Sep. 17, 2013; 9 pages.
Extended European Search Report corresponding to EP 14 15 9394.7, completed Apr. 16, 2014 and dated Apr. 29, 2014; 8 pages.
European Search Report corresponding to EP 10 01 2659.8, completed Dec. 21, 2010; dated Jan. 3, 2011 3 pages.
European Search Report corresponding to EP 10 01 2646.5, completed Feb. 11, 2011; dated Feb. 22, 2011.
Extended European Search Report corresponding to EP 14 15 1663.3 dated Jun. 7, 2016.
Supplementary European Search Report corresponding to EP 14 81 7036 dated Feb. 2, 2017.
European Search Report corresponding to EP 17 15 7259.7 dated May 10, 2017.
Chinese First Office Action corresponding to CN 201480037169.2 dated Jun. 29, 2017.
Chinese First Office Action corresponding to CN 201410418879.1 dated Jun. 29, 2017.
European Office Action corresponding to EP 14 17 8107.0 dated Oct. 12, 2017.
Australian Examination Report No. 1 corresponding to AU 2014200870 dated Oct. 26, 2017.
Chinese Second Office Action corresponding to CN 201410090675 dated Nov. 6, 2017.
Japanese Office Action corresponding to JP 2014-048652 dated Nov. 14, 2017.
Japanese Office Action corresponding to JP 2014-047708 dated Nov. 14, 2017.
Chinese Second Office Action corresponding to CN 2014103063407 dated Feb. 1, 2018.
Australian Examination Report No. 1 corresponding to AU 2014202970 dated Mar. 9, 2018.
Japanese Office Action corresponding to JP 2014-048652 dated Mar. 15, 2018.
Chinese Second Office Action corresponding to CN 201480077682.4 dated Mar. 21, 2018.
Australian Examination Report No. 1 corresponding to AU 2014202972 dated Mar. 27, 2018.
European Office Action corresponding to Patent Application EP 14 15 8946.5 dated Apr. 26, 2018.
Japanese Office Action corresponding to Patent Application JP 2014-132105 dated May 1, 2018.
Japanese Office Action corresponding to Patent Application JP 2014-047708 dated May 14, 2018.
Chinese Second Office Action corresponding to Patent Application CN 2014103559671 dated May 25, 2018.
Australian Examination Report No. 1 corresponding to Patent Application AU 2014302551 dated Jul. 16, 2018.
Japanese Office Action corresponding to Patent Application JP 2014-047708 dated Aug. 15, 2018.
Extended European Search Report dated Dec. 19, 2019 corresponding to counterpart Patent Application EP 19172130.7.

* cited by examiner

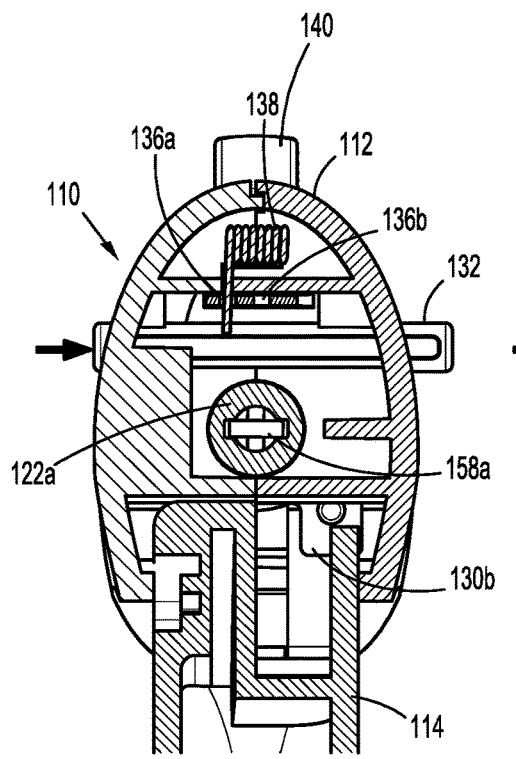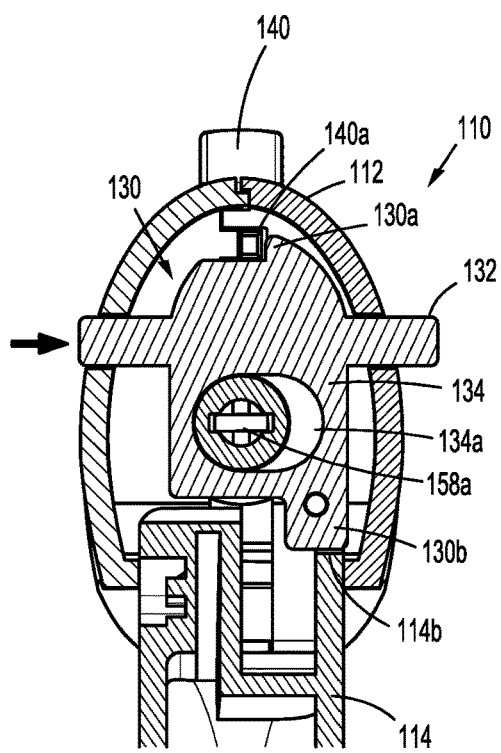
FIG. 8  FIG. 9
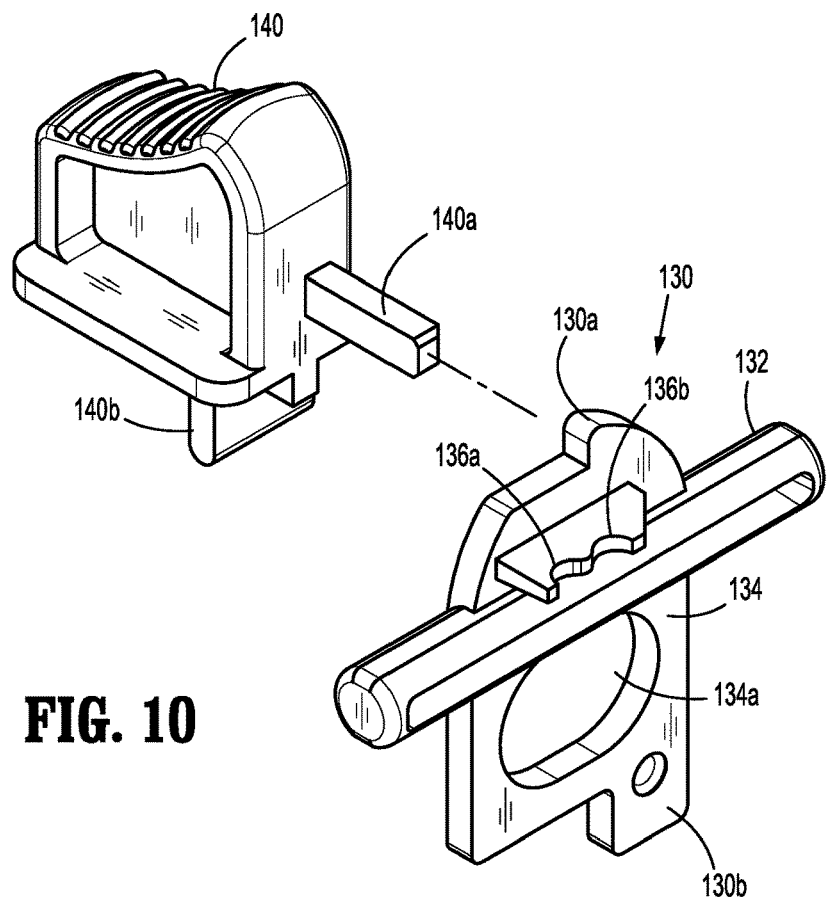
FIG. 10

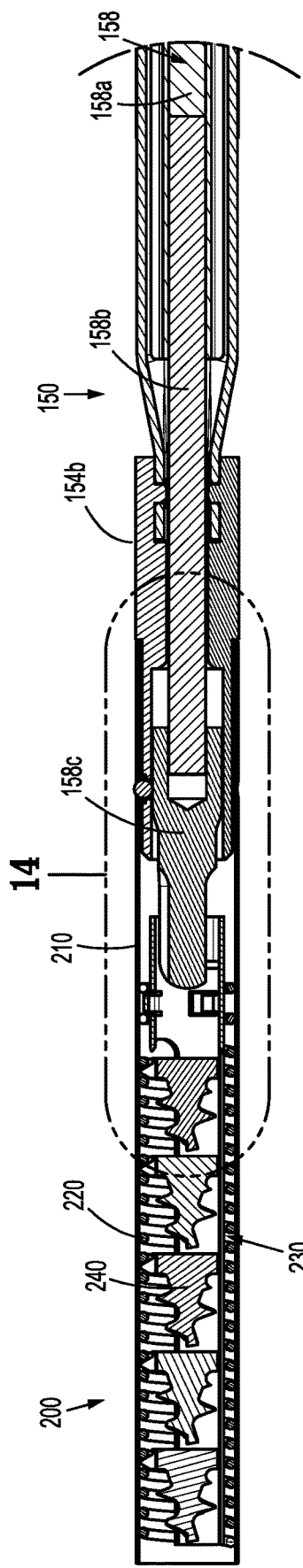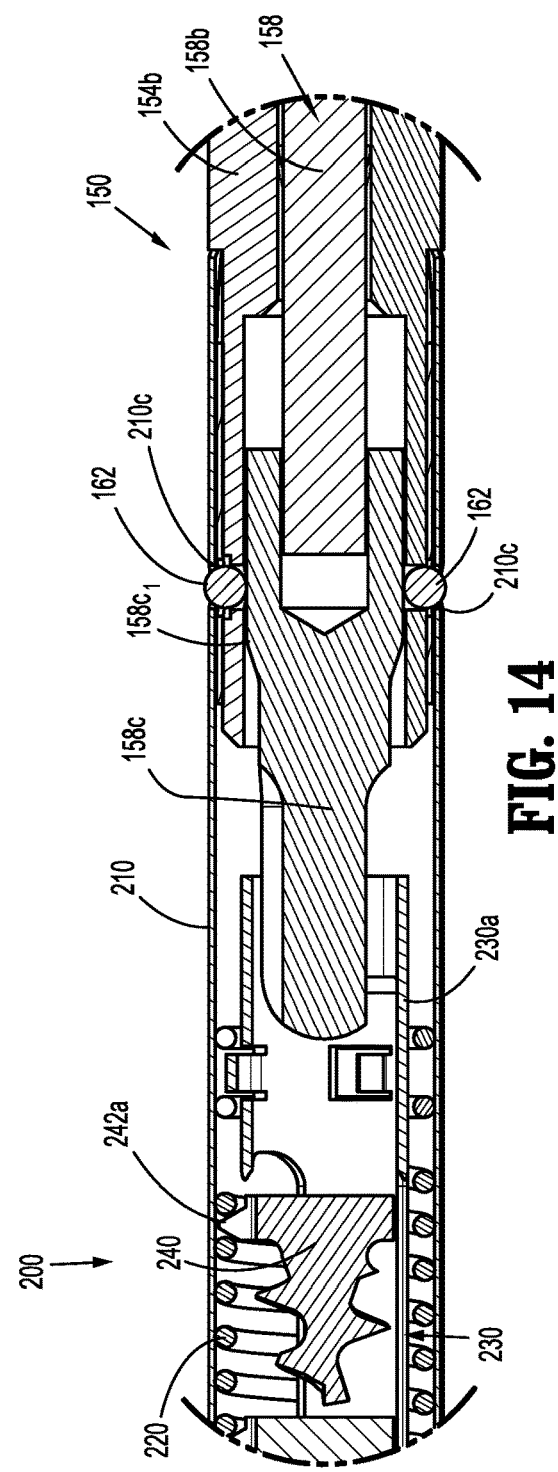

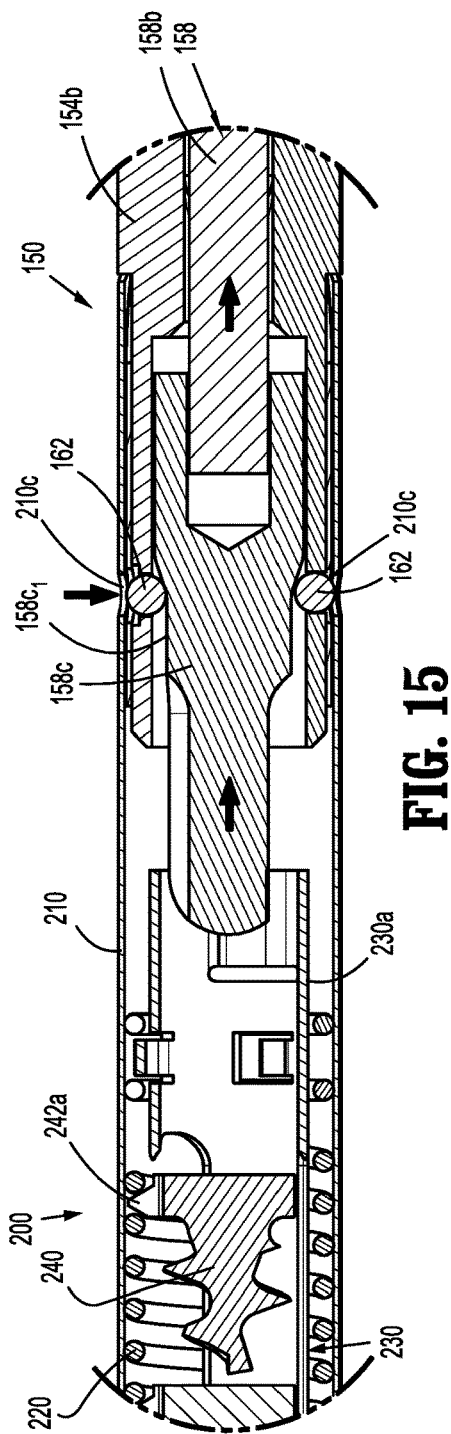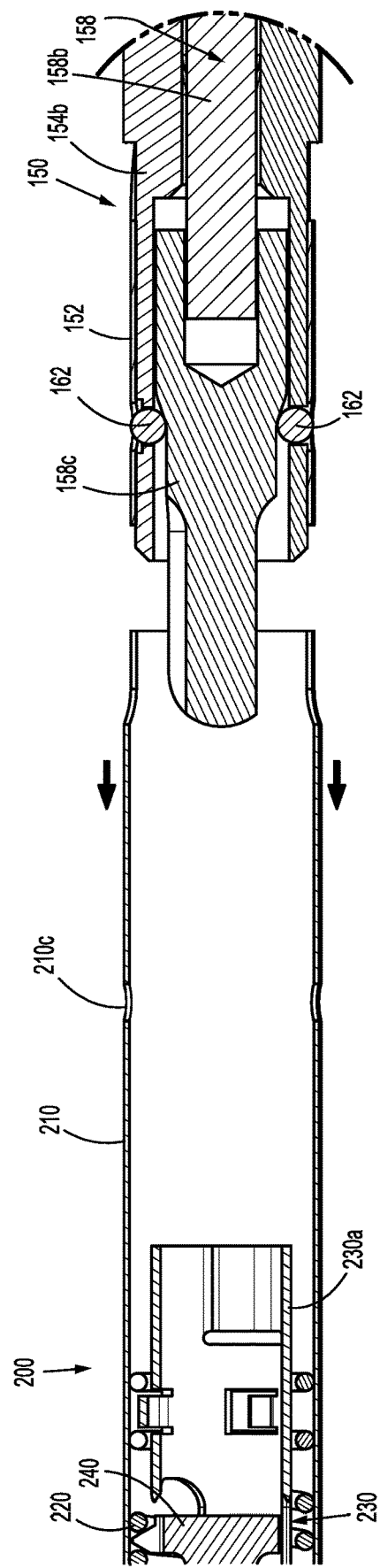

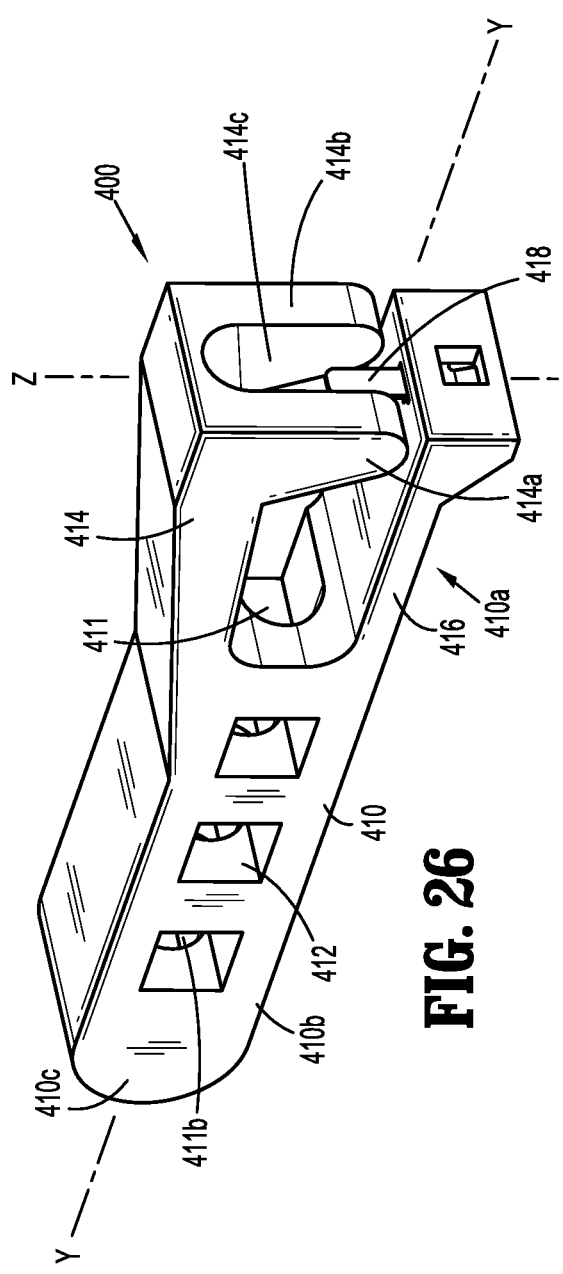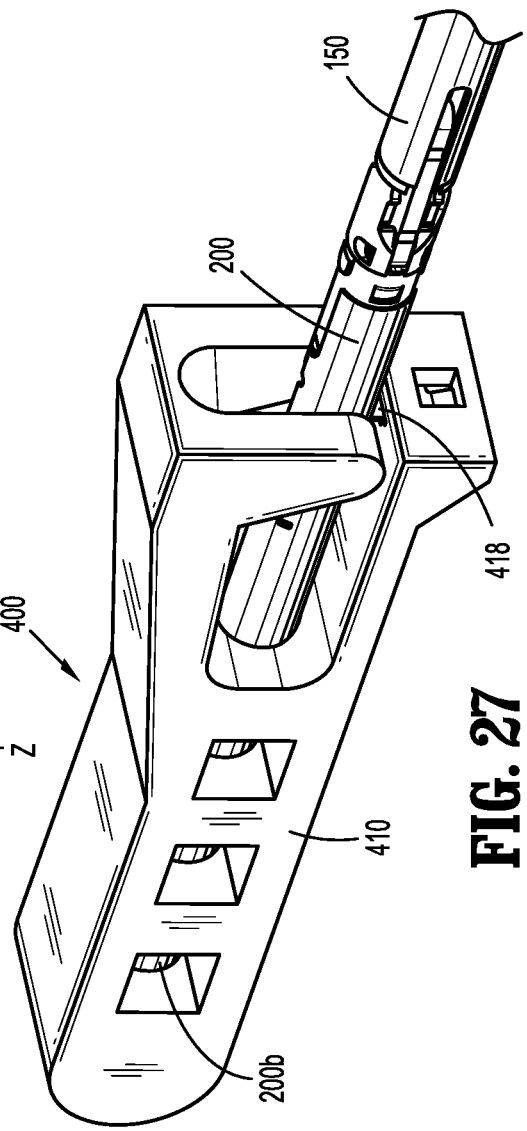

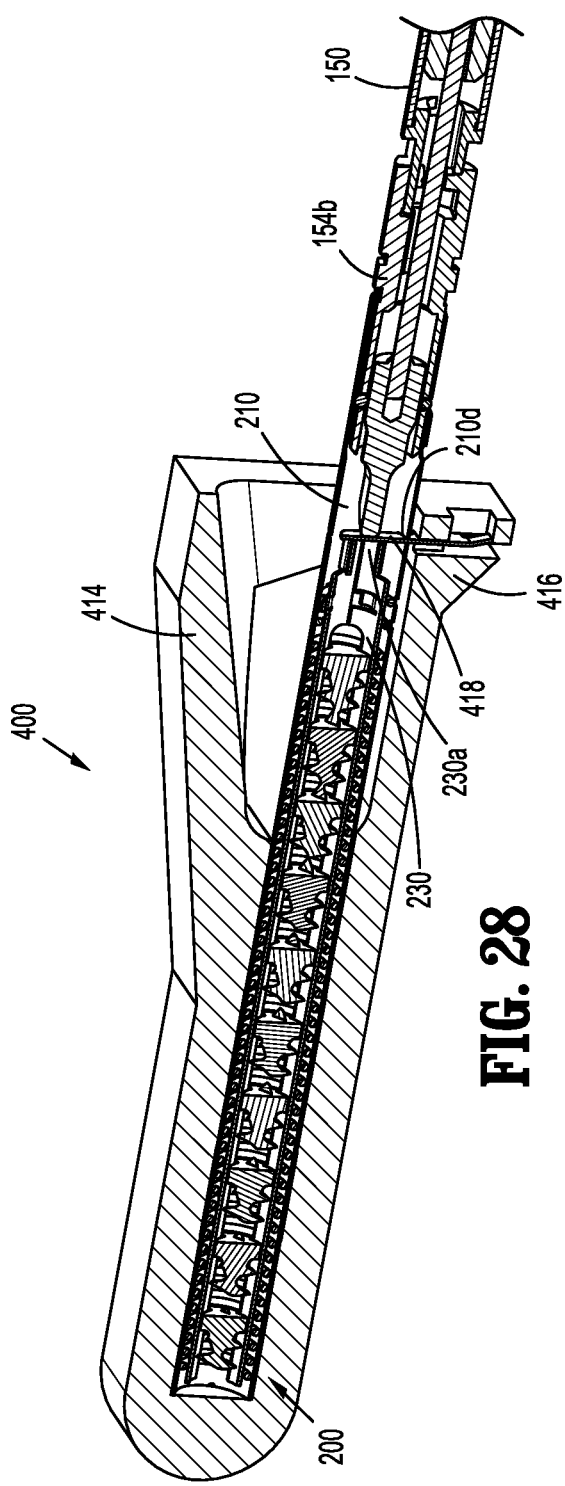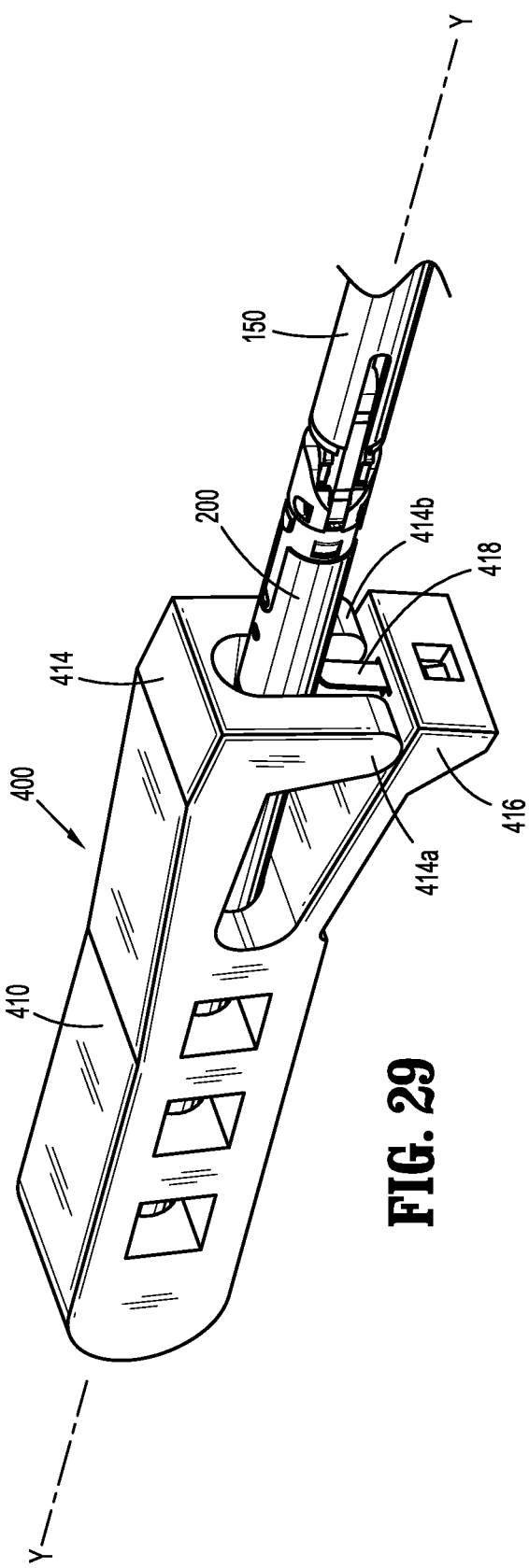

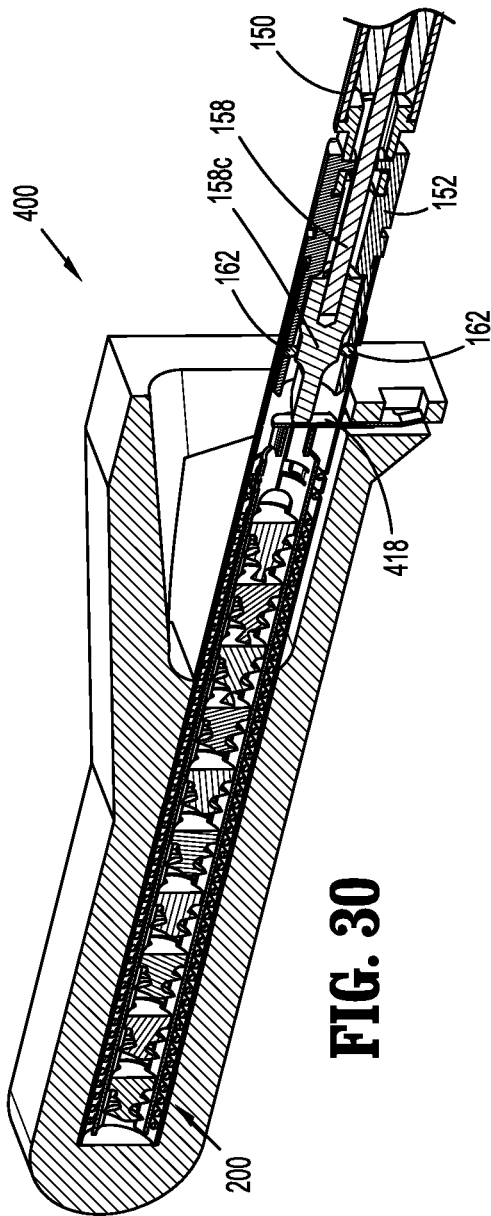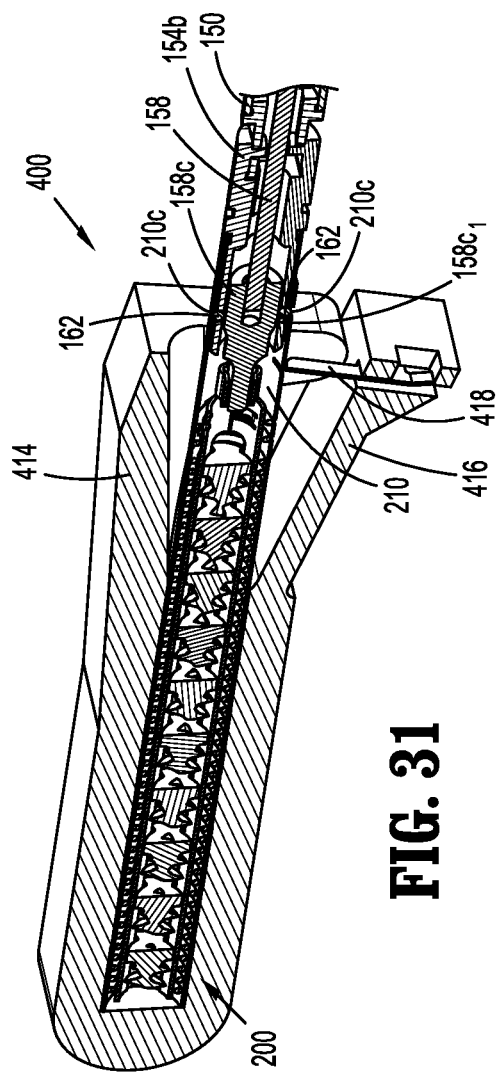

SHIPPING WEDGE FOR END EFFECTOR INSTALLATION ONTO SURGICAL DEVICES

CROSS-REFERENCE TO RELATED APPLICATION

This application claims the benefit of and priority to U.S. Provisional Patent Application No. 62/665,548 filed May 2, 2018, the entire disclosure of which is incorporated by reference herein.

TECHNICAL FIELD

The present disclosure relates to surgical devices and methods of using the same. More specifically, the present disclosure relates to shipping wedges for installing end effectors onto surgical fastener applying devices.

BACKGROUND

Various surgical procedures require devices capable of applying fasteners to tissue to form tissue connections or to secure objects to tissue. Minimally invasive, e.g., endoscopic or laparoscopic, surgical procedures are currently available to form these tissue connections or to secure objects to tissue. Laparoscopic and endoscopic procedures generally utilize long and narrow instruments capable of reaching remote regions within the body and are configured to form a seal with the incision or tube they are inserted through. Additionally, the devices are typically capable of being actuated remotely, that is, from outside the body.

During hernia repair, for example, it is often desirable to fasten a mesh to body tissue. Minimally invasive surgical techniques for hernia repair utilize surgical fasteners, e.g., surgical tacks, staples, and/or clips, to secure the mesh to the tissue to provide reinforcement and structure for encouraging tissue ingrowth. Surgical fasteners are often applied through an elongated device, such as a surgical fastener applying apparatus, for delivery to the mesh, and are manipulated from outside a body cavity.

Some surgical fastener applying apparatus include a reusable handle or actuator section and a removable and/or replaceable end effector that includes the surgical fasteners. The end effector may be provided with a safety device or shipping wedge during shipment and/or prior to use. Typically, the shipping wedge is removed after the end effector is installed onto the reusable handle. However, in some instances, the shipping wedge can be removed from the end effector prior to the end effector being assembled with the reusable handle. It would be desirable to provide shipping wedges that can facilitate the proper loading of an end effector onto a reusable handle.

SUMMARY

In accordance with an aspect of the present disclosure, a shipping wedge includes an elongated body extending along a longitudinal axis and defining a channel therethrough, and an arm disposed within a slot formed in a side wall of the elongate body. The arm includes a first end coupled to the side wall and a second end that is movable laterally with respect to the side wall.

The shipping wedge may include a handle extending transversely from the elongate body. The arm may include a projection extending from an inner surface of the arm. In some aspects, the projection of the arm includes a first surface extending laterally into the channel of the elongate body and/or a cam ramp tapering distally towards the inner surface of the arm. The shipping wedge may include a pair of guide walls extending transversely from the elongate body in substantially parallel and spaced relation relative to each other on opposed sides of the slot of the side wall. The elongate body of the shipping wedge may include a proximal portion defining a circumferential wall.

In accordance with another aspect of the present disclosure, a shipping wedge includes an elongate body extending along a longitudinal axis and defining a channel therethrough. A proximal portion of the elongate body includes a first arm extending proximally from a distal portion of the elongate body and a locking tab extending laterally into the channel of the elongate body.

In some aspects, the elongate body further includes a second arm disposed in spaced relation relative to the first arm. The locking tab may be secured to and extend from the second arm. The first arm may be biased to extend along an axis that is disposed at an angle with respect to the longitudinal axis of the elongate body and the second arm may be biased to extend along an axis that is substantially parallel to the longitudinal axis. The first arm may be movable to a deflected position extending along an axis substantially parallel to the longitudinal axis.

The first arm may include a pair of fingers extending laterally towards the second arm. The pair of fingers may be disposed in spaced relation relative to each other and define a slot therebetween. The locking tab may extend into the slot. When the first arm is disposed in the deflected position, the pair of fingers may press against and move the second arm to a deflected position extending along an axis that is disposed at an angle with respect to the longitudinal axis.

In some aspects, the first arm is biased to extend along an axis that is substantially parallel to the longitudinal axis. The first arm may include a latch extending from an inner surface of the first arm. The latch may include a first surface extending laterally into the channel of the elongate body and a cam ramp tapering from the first surface proximally towards the inner surface of the first arm. The first arm may include a slit defined therethrough and the locking tab may be positioned through the slit and slidably movable therein between a first position in which a first end of the locking tab is disposed within the channel of the elongate body and a second position in which the first end of the locking tab is disposed within the slit. The locking tab may include a second end extending laterally outward of the first arm. The second end may define a pull tab for moving the locking tab between the first and second positions.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein:

FIG. 8 is a cross-sectional view as taken through 8-8 of FIG. 5, illustrating a button of a handle housing of the endoscopic surgical device in a second position;

FIG. 9 is a cross-sectional view as taken through 9-9 of FIG. 5;

FIG. 10 is a perspective view of a button and a slider of a handle housing of the endoscopic surgical device of FIG. 1;

FIG. 13 is a cross-sectional view of a distal portion of the endoscopic surgical device of FIG. 1, as taken through 13-13 of FIG. 2;

FIG. 14 is an enlarged view of the indicated area of detail of FIG. 13;

FIG. 15 is a longitudinal, cross-sectional view of an end effector and an endoscopic assembly of the endoscopic surgical device of FIG. 1, illustrating the end effector decoupled from the endoscopic assembly;

FIG. 16 is a longitudinal, cross-sectional view of the end effector and the endoscopic assembly of the endoscopic surgical device of FIG. 1, illustrating the end effector decoupled from the endoscopic assembly;

FIG. 26 is a rear, perspective view of a shipping wedge in accordance with another embodiment of the present disclosure;

FIG. 27 is a rear, perspective view of the shipping wedge of FIG. 26, installed on an end effector;

FIG. 28 is a cross-sectional view of the shipping wedge and the end effector of FIG. 27, illustrating the shipping wedge in a locked configuration;

FIG. 29 is a rear, perspective view of the shipping wedge and the end effector of FIG. 27, illustrating the shipping wedge in an unlocked configuration;

FIG. 30 is a cross-sectional view of the shipping wedge and the end effector of FIG. 27, illustrating the shipping wedge in a locked configuration during installation on an endoscopic assembly of the endoscopic surgical device of FIG. 1;

FIG. 31 is a cross-sectional view of the shipping wedge and the end effector of FIG. 27, illustrating the shipping wedge in an unlocked configuration during installation on an endoscopic assembly of the endoscopic surgical device of FIG. 1;

DETAILED DESCRIPTION

Figure 1:
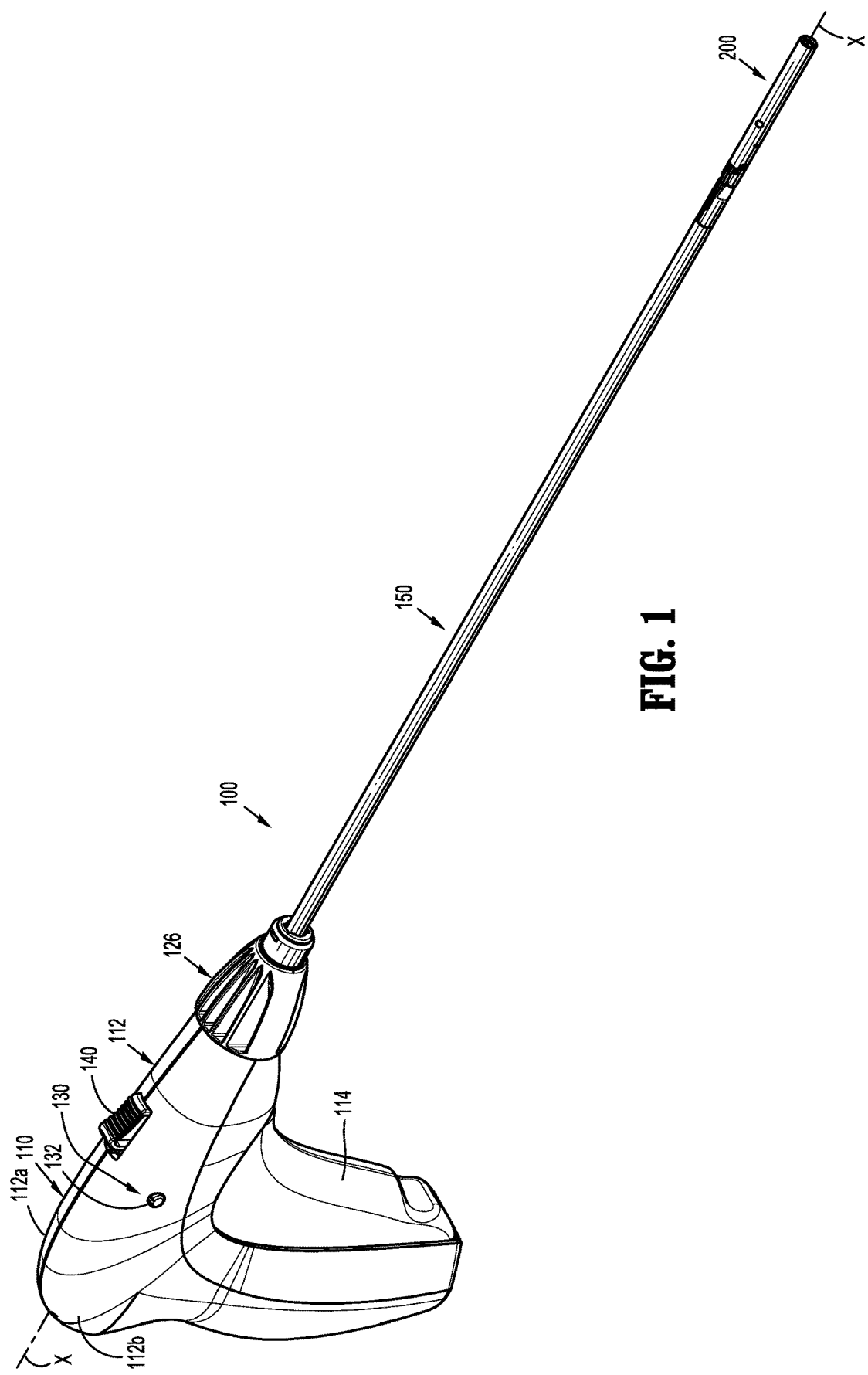
FIG. 1 is a perspective view of an endoscopic surgical device in accordance with an embodiment of the present disclosure.

Embodiments of the presently disclosed devices are described in detail with reference to the drawings, in which like reference numerals designate identical or corresponding elements in each of the several views. As used herein, the term "distal" refers to that portion of a system, a device, or a component thereof that is farther from a user, while the term "proximal" refers to that portion of the system, the device, or the component thereof that is closer to the user.

Non-limiting examples of endoscopic surgical devices according to the present disclosure include manual, mechanical and/or electromechanical surgical tack appliers (e.g., tackers) and the like. For a more detailed description of endoscopic surgical devices and components thereof that can be used with, or adapted for use with, a shipping wedge of the present disclosure, reference can be made to U.S. Patent Appl. Pub. Nos. 2016/0166255 and 2016/0270835, the entire content of each of which is hereby incorporated by reference herein.

Figure 2:
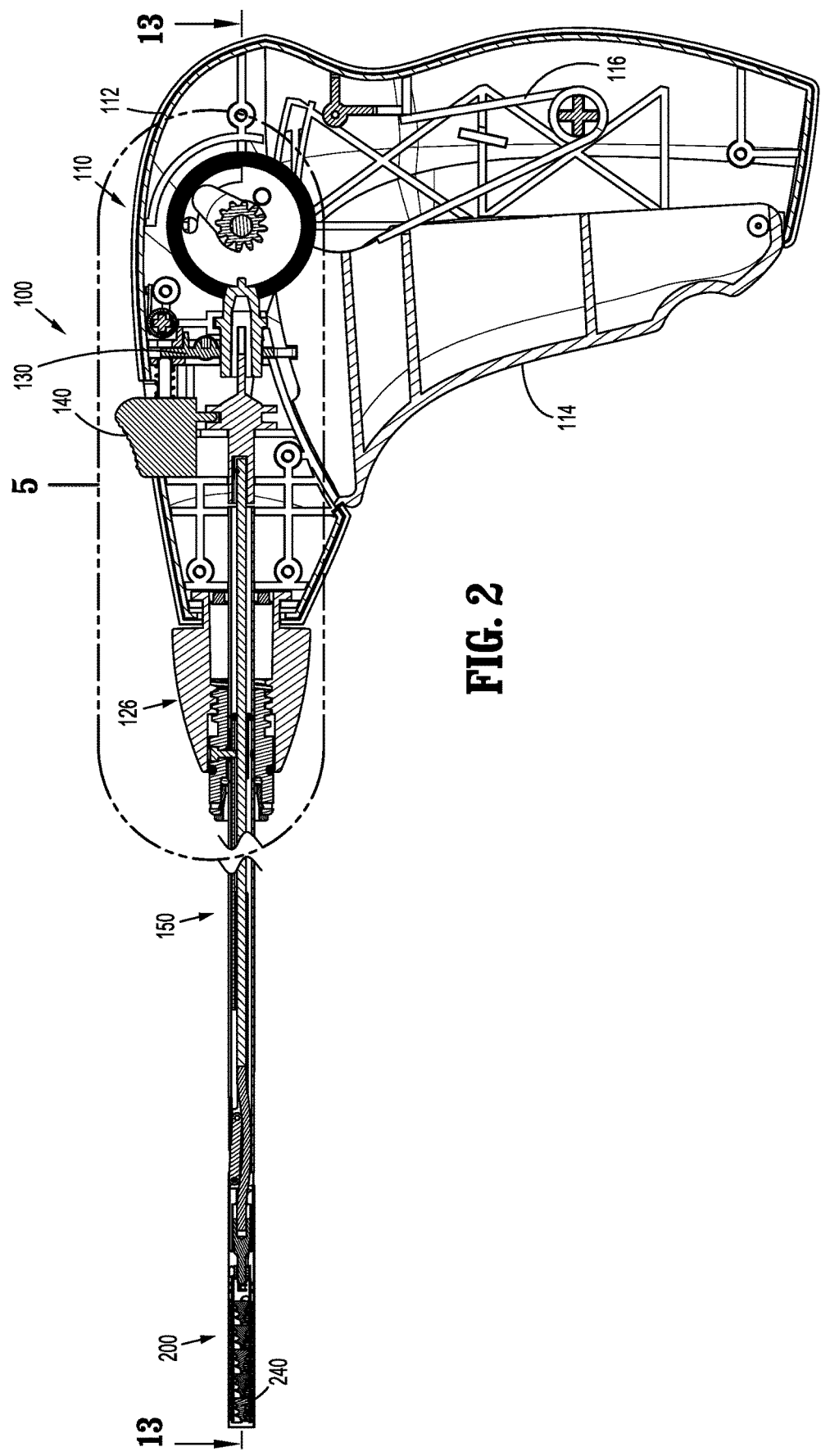
FIG. 2 is a longitudinal, cross-sectional view of the endoscopic surgical device of FIG. 1.

Referring now to FIGS. 1 and 2, an exemplary endoscopic surgical device, in the form of an endoscope surgical tack applier or tacker, is shown generally as 100. The surgical tack applier 100 includes a handle assembly 110 and an endoscopic or anchor retaining/advancing assembly 150 extending from the handle assembly 110 along a longitudinal axis "X". An end effector 200 is selectively detachable/attachable from/to the endoscopic assembly 150.

The handle assembly 110 includes a handle housing 112 formed from a first half-section 112a and a second half section 112b joined to one another. The handle assembly 110 includes a trigger 114 pivotably connected to the handle housing 112 and a biasing member 116 disposed within the handle housing 112 that is configured to maintain the trigger 114 in an extended or un-actuated position and to have a spring constant sufficient to return the trigger 114 to the un-actuated position after a driving or firing stroke.

Figure 3:
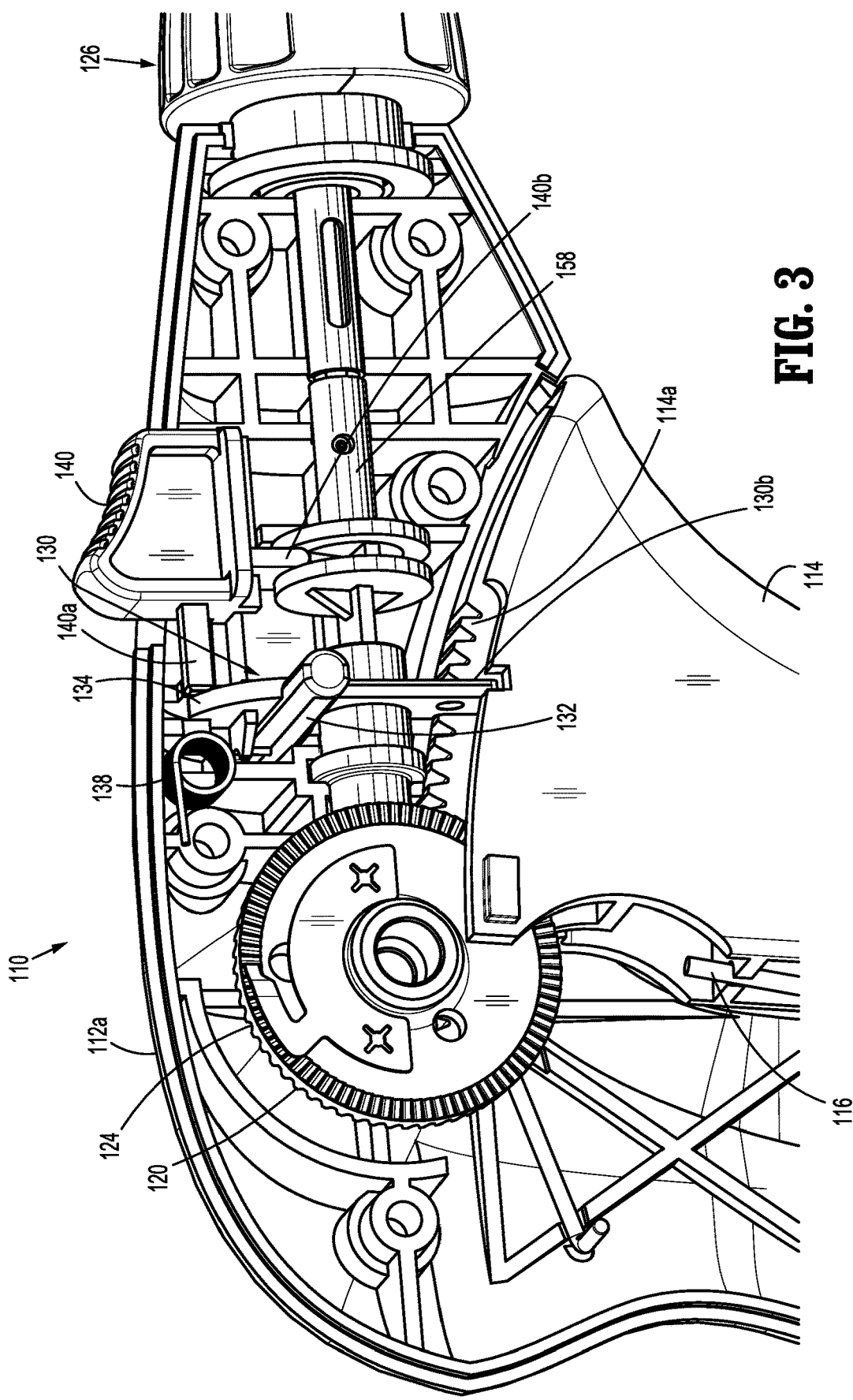
FIG. 3 is a rear, perspective view, with a first housing half-section removed therefrom, of a handle assembly of the endoscopic surgical device of FIG. 1.
Figure 4:
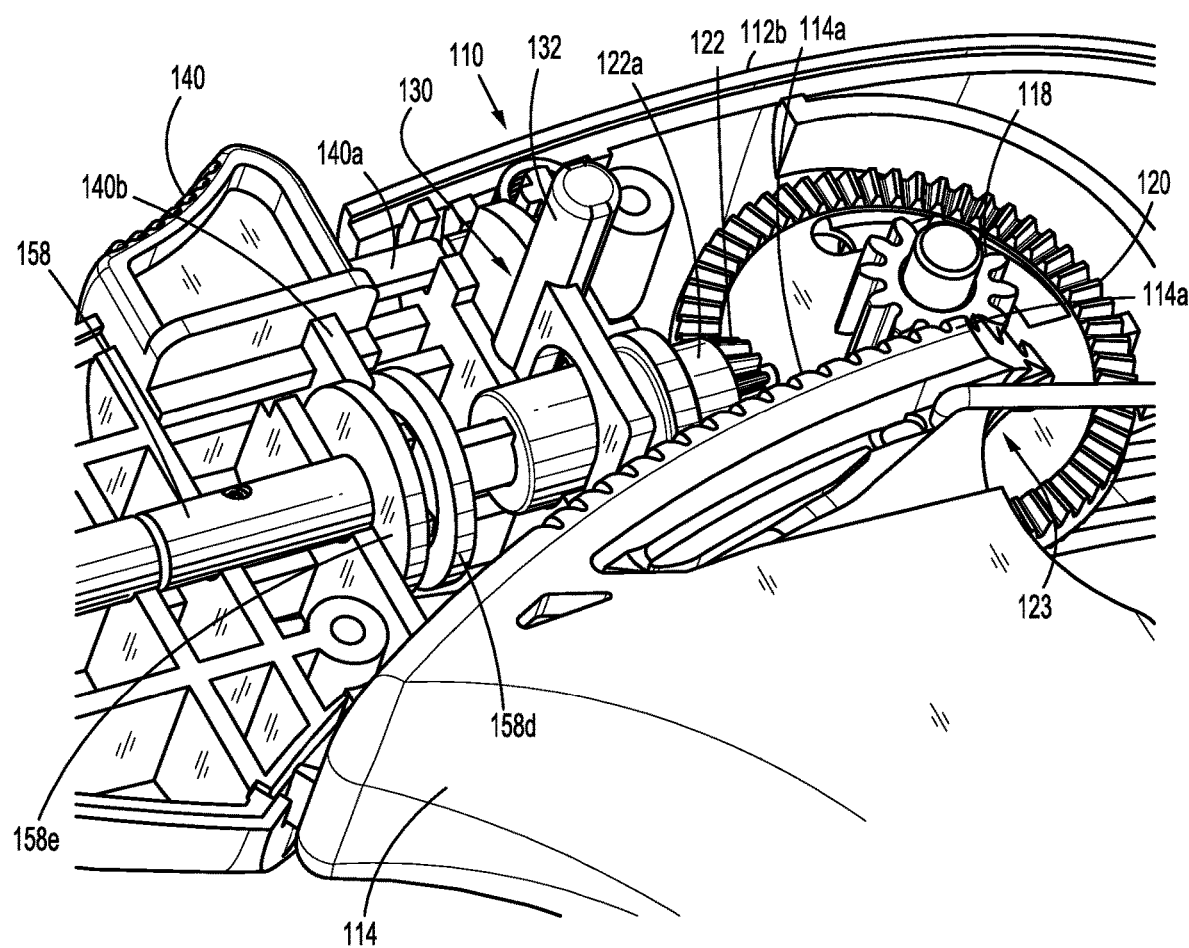
FIG. 4 is a front, perspective view, with a second housing half-section removed therefrom, of a handle assembly of the endoscopic surgical device of FIG. 1.
Figure 5:
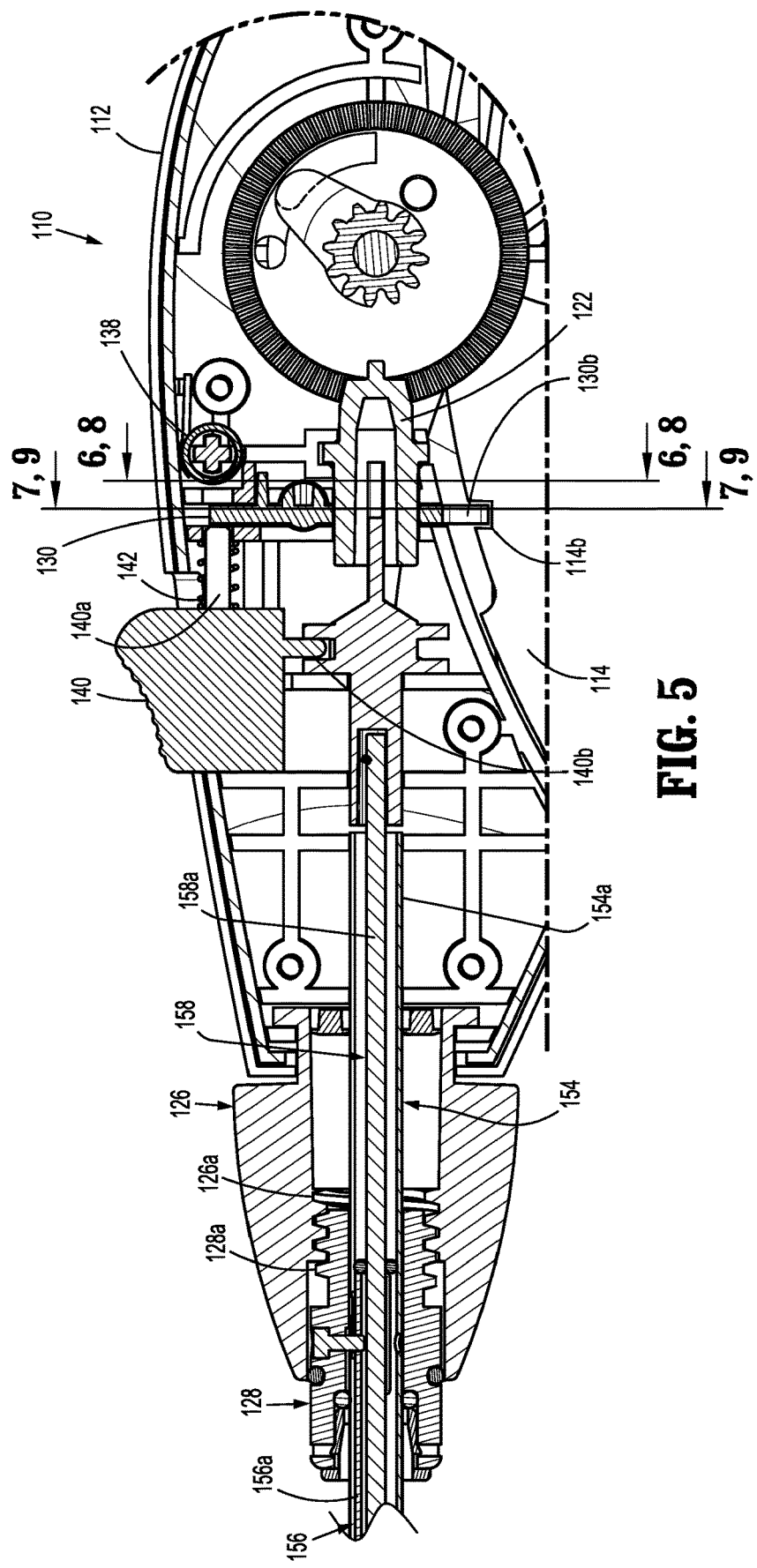
FIG. 5 is an enlarged view of the indicated area of detail of FIG. 2.

As shown in FIGS. 3 and 4, the trigger 114 defines a gear rack 114a formed thereon that is configured for operative engagement with a pinion gear 118 rotatably supported in the handle housing 112. The handle assembly 110 further includes a first bevel gear 120 disposed within the handle housing 112 that is operatively engaged/associated with the pinion gear 118 and a second or pinion-bevel gear 122 operatively engaged or meshed with the first bevel gear 120. The pinion-bevel gear 122 is secured to a proximal end of an inner shaft assembly 158 of the endoscopic assembly 150.

In use, upon squeezing of the trigger 114, the gear rack 114a thereof causes the pinion gear 118 to rotate in a first direction. Rotation of the pinion gear 118 in the first direction results in rotation of the first bevel gear 120 in a first direction and, in turn, rotation of the pinion-bevel gear 122 in a first direction. As the pinion-bevel gear 122 is rotated in the first direction, the pinion-bevel gear 122 transmits the rotation to the inner shaft assembly 158 of the endoscopic assembly 150.

The handle assembly 110 is further provided with a timing system 123 that prevents the trigger 114 from returning to the un-actuated position if the trigger 114 is released after a partial squeeze, and a ratchet mechanism 124 that inhibits or prevents the inner shaft assembly 158 from backing-out or reversing after an anchor or fastener 240 (see e.g., FIG. 2) of the end effector 200 has been at least partially driven into tissue.

As shown in FIGS. 1-3 and 5, the handle assembly 110 includes an articulation knob 126 rotatably supported on the handle housing 112. The articulation knob 126 defines an inner helical thread 126a that meshingly receives or engages an outer thread 128a of a connection nut 128 that is non-rotatably connected to a proximal tube portion 156a of an inner articulation tube assembly 156 of the endoscopic assembly 150. Rotation of the articulation knob 126 in first or second directions results in articulating or straightening of the endoscopic assembly 150.

Figures 6, 7:
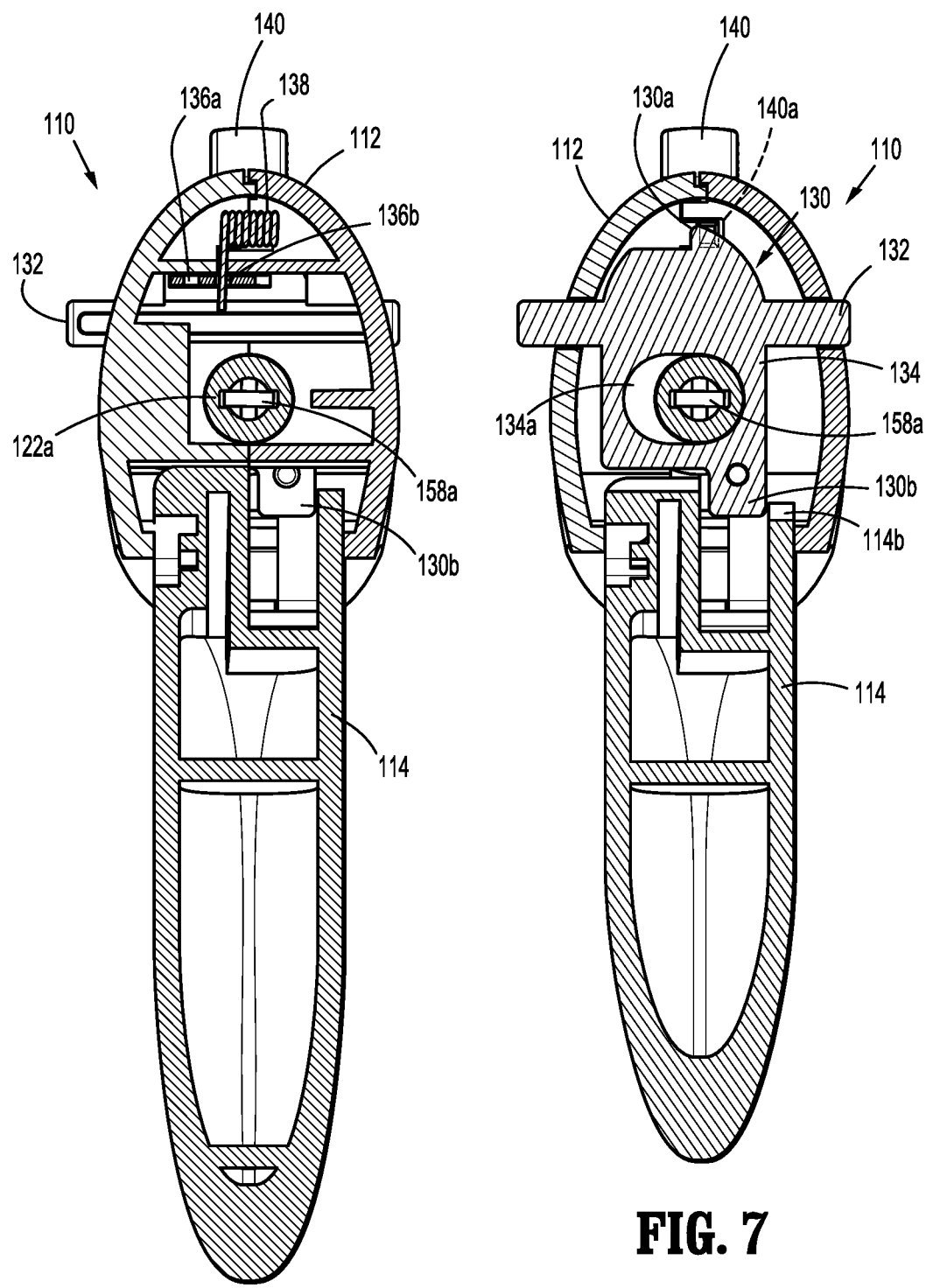
FIG. 6 is a cross-sectional view as taken through 6-6 of FIG. 5, illustrating a button of a handle housing of the endoscopic surgical device in a first position.
FIG. 7 is a cross-sectional view as taken through 7-7 of FIG. 5.

As shown in FIGS. 1-5, the handle assembly 110 includes a button 130 supported on the handle housing 112. The button 130 is configured to permit and inhibit actuation of the trigger 114, and to effectuate a loading/retention and a release/removal of an end effector 200 to the endoscopic assembly 150. The button 130 includes a pin 132 slidably supported in the handle housing 112 and oriented in a direction orthogonal to the longitudinal axis "X" of the endoscopic assembly 150. The pin 132 has a length such that when the button 130 is in a first position, as shown in FIGS. 6 and 7, a first end of the pin 132 extends from a first side of handle housing 112, and when the button 130 is in a second position, as shown in FIGS. 8 and 9, a second end of the pin 132 extends from a second side of handle housing 112.

With reference now to FIGS. 6-11, the button 130 includes a plate 134 supported on and connected to the pin 132. The plate 134 defines an elongate slot 134a therein, through which a stem 122a of the pinion-bevel gear 122 extends. The elongate slot 134a of plate 134 defines a major axis which is parallel relative to the longitudinal axis of the pin 132. In use, as the pin 132 is moved between the first position and the second position, the plate 134 is moved between respective first and second positions.

The button 130 further includes a first detent or recess 136a defined in the plate 134 that is engaged by a biasing member 138 (e.g., a plunger spring or torsion spring) when the button 130 is in the first position, and a second detent or recess 136b defined in the plate 134 that is engaged by the biasing member 138 when the button 130 is in the second position. The engagement of the biasing member 138 in either the first detent 136a or the second detent 136b of the button 130 functions to help maintain the button 130 in either the first or second position.

The button 130 also includes a first wall 130a extending from the plate 134, and a second wall 130b extending from the plate 134. In use, when the button 130 is in the first position, the first wall 130a thereof blocks or inhibits movement of a load/release slider 140, and when the button 130 is in the second position, the first wall 130a thereof permits movement of load/release slider 140. Similarly, in use, when the button 130 is in the second position (only achievable when the trigger 114 is in a fully un-actuated or home position), the second wall 130b thereof blocks or inhibits actuation of the trigger 114 by the second wall 130b extending into a notch 114b of the trigger 114; and when the button 130 is in the first position, the second wall 130b is clear of the notch 114b of the trigger 114 to permit actuation of the trigger 114.

With continued reference to FIGS. 6-11, the handle assembly 110 includes a load/release slider 140 (also referred to herein as a slider) slidably supported on the handle housing 112. The slider 140 is configured to effectuate a loading/retention and a release/removal of an end effector 200 (see e.g., FIG. 1), in the form of a single use loading unit (SULU) or disposable loading unit (DLU), as will be discussed in greater detail below. The slider 140 includes a first stem 140a extending proximally therefrom and towards button 130. Specifically, the first stem 140a of the slider 140 is in axial registration with the first wall 130a extending from the plate 134 of the button 130 when the button 130 is in the first position (see e.g., FIG. 7), and out of axial registration with the first wall 130a of the button 130 when the button 130 is in the second position (see e.g., FIG. 9).

Figure 11:
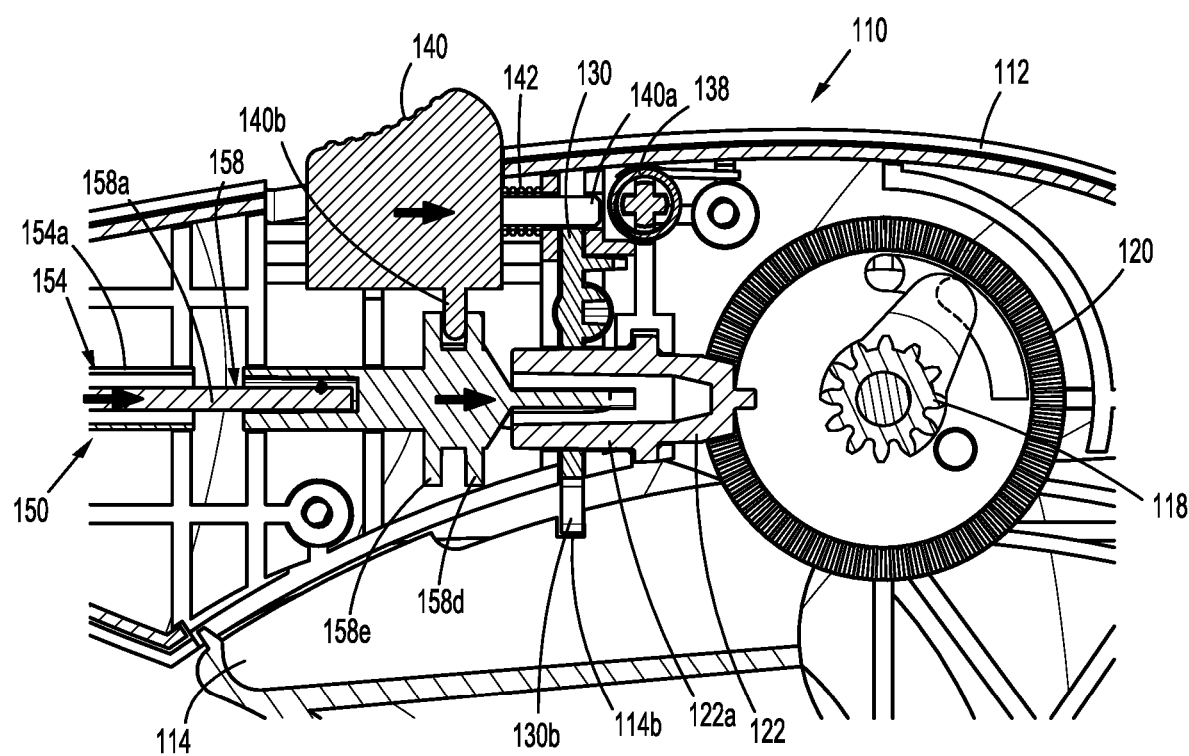
FIG. 11 is an enlarged view of the handle assembly shown in FIG. 4, illustrating an operation of a slider.
Figure 12:
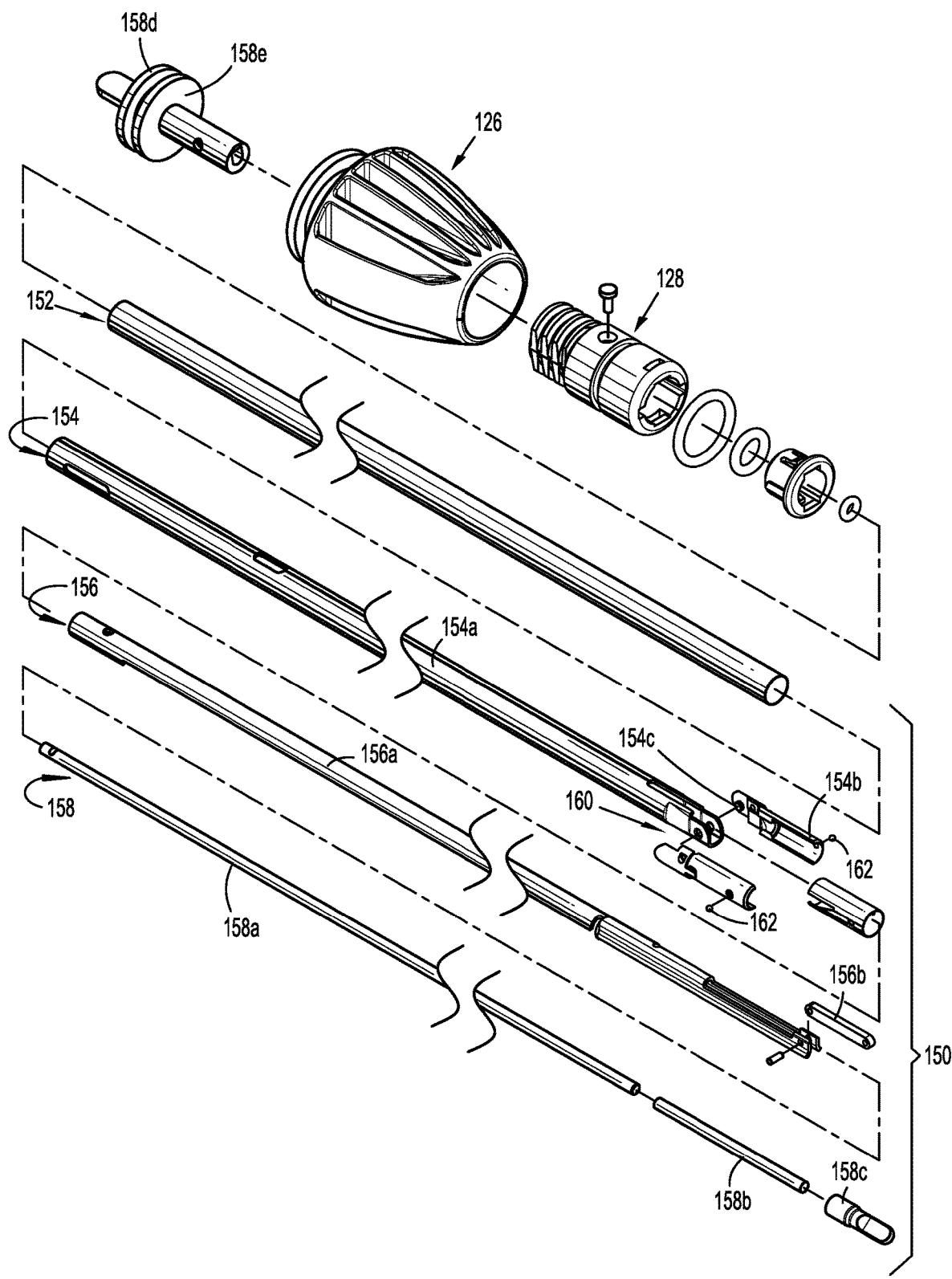
FIG. 12 is a perspective view, with parts separated, of an endoscopic assembly of the endoscopic surgical device of FIG. 1.

The slider 140 further includes a second stem 140b extending therefrom in a direction toward the inner shaft assembly 158 of the endoscopic assembly 150. As shown in FIG. 11, the inner shaft assembly 158 supports a pair of axially spaced apart proximal and distal radial flanges 158d, 158e which bookend the second stem 140b of the slider 140.

In use, when the button 130 is in the second position (wherein trigger 114 is locked in the fully un-actuated position) such that the first stem 140a of the slider 140 is out of axial registration with the first wall 130a of the button 130, the slider 140 is free to move between a first or distal position and a second or proximal position. As the slider 140 is moved from the first position to the second position thereof, the second stem 140b of the slider 140 exerts a force on the proximal radial flange 158d of the inner shaft assembly 158 to urge the inner shaft assembly 158 proximally from a respective first position to a respective second position. It follows that as the slider 140 is moved from the second position to the first position thereof, the second stem 140b of the slider 140 exerts a force on the distal radial flange 158e of the inner shaft assembly 158 to urge the inner shaft assembly 158 distally from the respective second position to the respective first position. The slider 140 may be biased in the first or distal portion by a biasing member 142.

Turning now to FIGS. 5 and 12-16, the endoscopic assembly 150 includes an outer tube 152, an outer support tube assembly 154 disposed within outer tube 152, an inner articulation tube assembly 156, and an inner shaft assembly 158. The outer support tube assembly 154 includes a proximal support tube portion 154a secured to and extending from the handle housing 112, and a distal support tube portion 154b pivotally connected to the proximal support tube portion 154a by a pivot pin 154c at an articulation joint 160.

The distal support tube portion 154b supports ball detents 162 in an outer surface thereof. The ball detents 162 function to selectively secure and retain an end effector 200 to the endoscopic assembly 150. In use, as will be discussed in greater detail below, the ball detents 162 are acted on by an outer camming surface/relief $158c_1$ of a coupling member 158c of the inner shaft assembly 158 to move the ball detents 162 radially outward when the inner shaft assembly 158 is in a distal position.

The inner articulation tube assembly 156 includes a proximal tube portion 156a concentrically and slidably disposed within the proximal tube portion 154a of the outer support tube assembly 154. A proximal end of the proximal tube portion 156a is non-rotatably connected to the connection nut 128. The inner articulation tube assembly 156 further includes an articulation link 156b having a proximal end pivotally connected to a distal end of the proximal tube portion 154a, and a distal end pivotally connected to the distal tube portion 154b of the outer support tube assembly 154. Upon axial translation of the proximal tube portion 156a, for example, in a proximal direction due to rotation of the articulation knob 126 or a distal direction due to a distal movement of the slider 140, the proximal tube portion 156a acts (e.g., pulls or pushes) on the articulation link 156b to cause the articulation link 156b to translate in a respective proximal or distal direction which, in turn, acts on the distal tube portion 154b to cause the distal tube portion 154b to pivot about a pivot axis of the pivot pin 154c which, in turn, causes the end effector 200 to be moved to an articulated or non-articulated orientation relative to the longitudinal axis "X" of the endoscopic assembly 150.

With continued reference to FIGS. 5 and 12-16, the inner shaft assembly 158 includes a proximal rigid shaft portion 158a, a distal flexible shaft portion 158b non-rotatably connected to and extending from a distal end of the proximal rigid shaft portion 158a, and a coupling member 158c non-rotatably connected to a distal end of the distal flexible shaft portion 158b. The pinion-bevel gear 122 is non-rotatably connected to a proximal end of the proximal rigid shaft portion 158a of the inner shaft assembly 158. The inner shaft assembly 158 is configured such that the distal flexible shaft portion 158b extends across and beyond the articulation joint 160.

The coupling member 158c is rotatably and slidably supported in the distal support tube portion 154b of the outer support tube assembly 154 so as to accommodate and/or account for variations in length of the distal flexible shaft portion 158b when the distal flexible shaft portion 158b is in a flexed condition. The coupling member 158c is substantially tongue shaped and extends in a distal direction distally from the distal support tube portion 154b of the outer support tube assembly 154. The coupling member 158c is configured for non-rotatable connection to an inner tube 230 of the end effector 200, as will be discussed in greater detail below.

The inner actuation shaft assembly 158 is configured to perform at least a pair of functions, a first function relating to the securing and release of an end effector 200 to the distal support tube portion 154b of the outer support tube assembly 154 upon an axial translation thereof, and a second function relating to the firing of the anchors 240 from the end effector 200 when the end effector 200 is coupled to the distal tube portion 154b of the outer support tube assembly 154 upon a rotation thereof.

Figure 17:
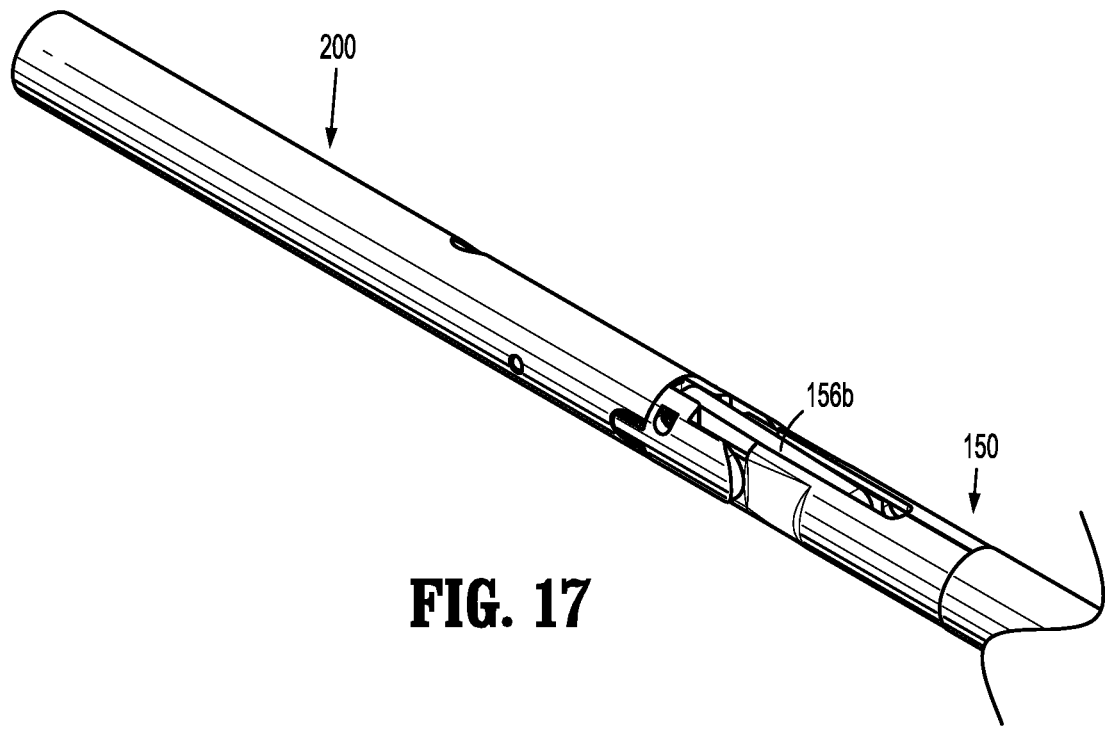
FIG. 17 is an enlarged view of an end effector and a distal end portion of an endoscopic assembly of the endoscopic surgical device of FIG. 1.
Figure 18:
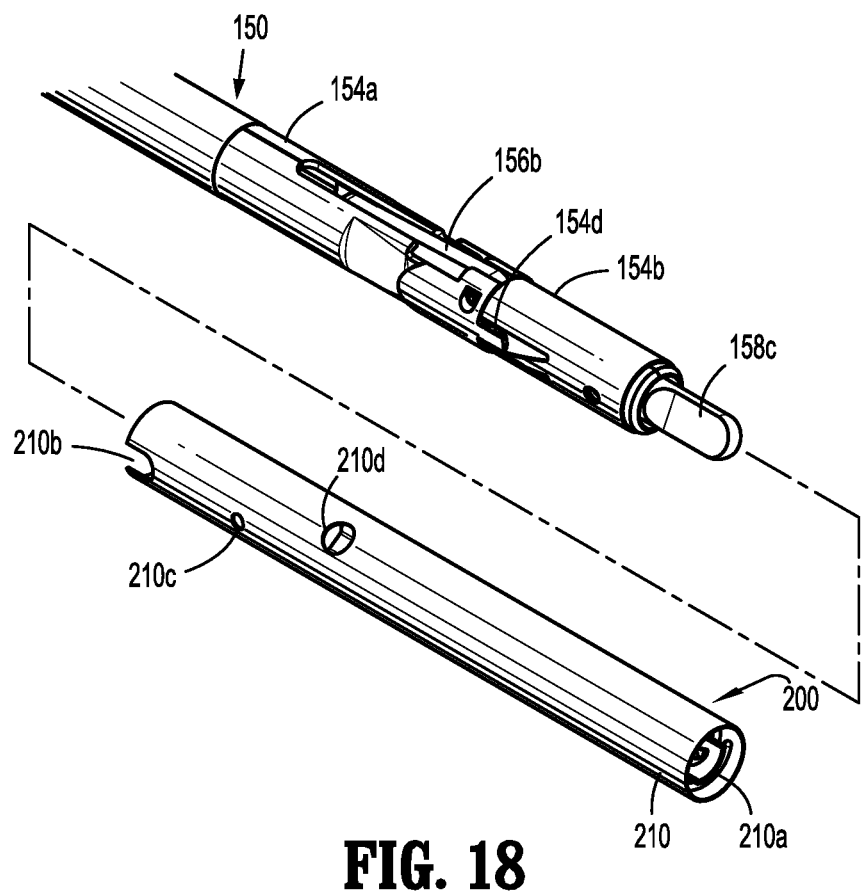
FIG. 18 is a perspective view of the distal end portion of the endoscopic surgical device of FIG. 1, with an end effector shown separated therefrom.

Turning now to FIGS. 17 and 18, the end effector 200, in the form of a SULU or DLU, is shown and will be described herein. The end effector 200, as mentioned above, is selectively connectable to the distal tube portion 154b of the outer support tube assembly 154 of the endoscopic assembly 150.

The end effector 200 includes an outer tube 210 defining a lumen 210a therethrough, and is configured and dimensioned (e.g., substantially rectangular or dog bone shaped) to receive the distal support tube portion 154b and the coupling member 158c of the endoscopic assembly 150 therein. The outer tube 210 defines a proximal key slot 210b for engagement with a key 154d formed in the distal tube portion 154b of the outer support tube assembly 154. In use, when the end effector 200 is connected to the distal tube portion 154b of the outer support tube assembly 154, the key slot 210b and the key 154d engage with one another to properly align the end effector 200 and the endoscopic assembly 150 to one another.

Figure 19:
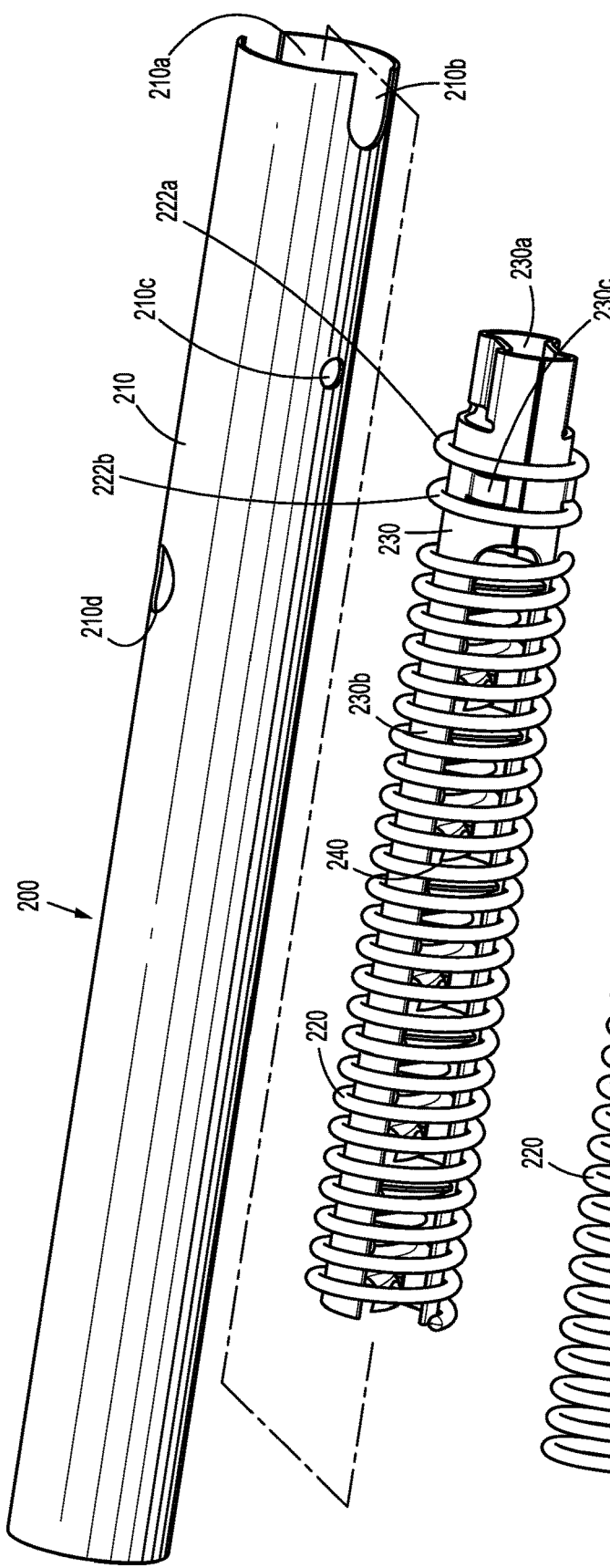
FIG. 19 is a perspective view of the end effector of FIG. 18, with an outer tube separated therefrom.
Figure 20:
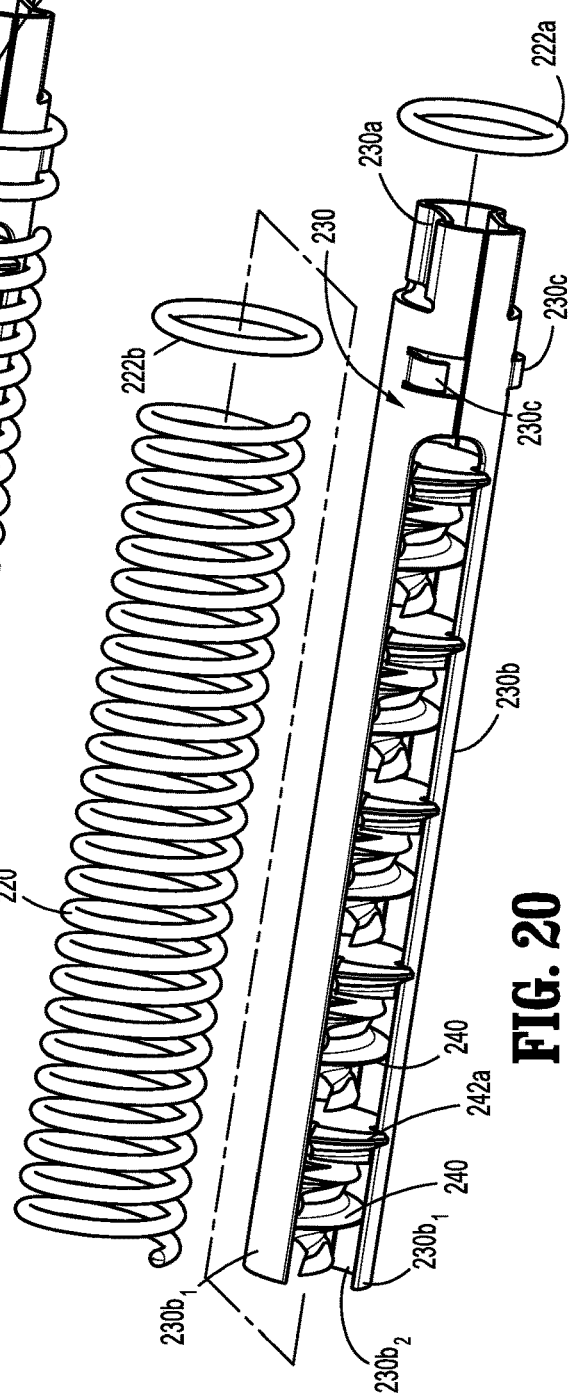
FIG. 20 is a perspective view of the end effector of FIG. 18, with an outer tube removed therefrom and with parts separated.

As shown in FIGS. 19 and 20, the end effector 200 further includes a spiral or coil 220 fixedly disposed within a distal portion of the outer tube 210. A pair of axially spaced apart retention rings 222a, 222b is also fixedly disposed within the outer tube 210 at a location proximal of the coil 220.

The end effector 200 also includes an inner tube 230 rotatably disposed within the coil 220. The inner tube 230 defines a lumen therethrough, and includes a proximal end portion 230a and a splined distal end portion 230b. The proximal end portion 230a of the inner tube 230 is configured and dimensioned to slidably receive the coupling member 158c of the endoscopic assembly 150 therein. The inner tube 230 includes a plurality of retention tabs 230c projecting radially outward therefrom and which snap beyond one of the pair of retention rings 222a, 222b, when the inner tube 230 is assembled with the outer tube 210. In this manner, the outer tube 210 and the inner tube 230 are axially fixed and yet rotatable relative to one another.

Figure 21:
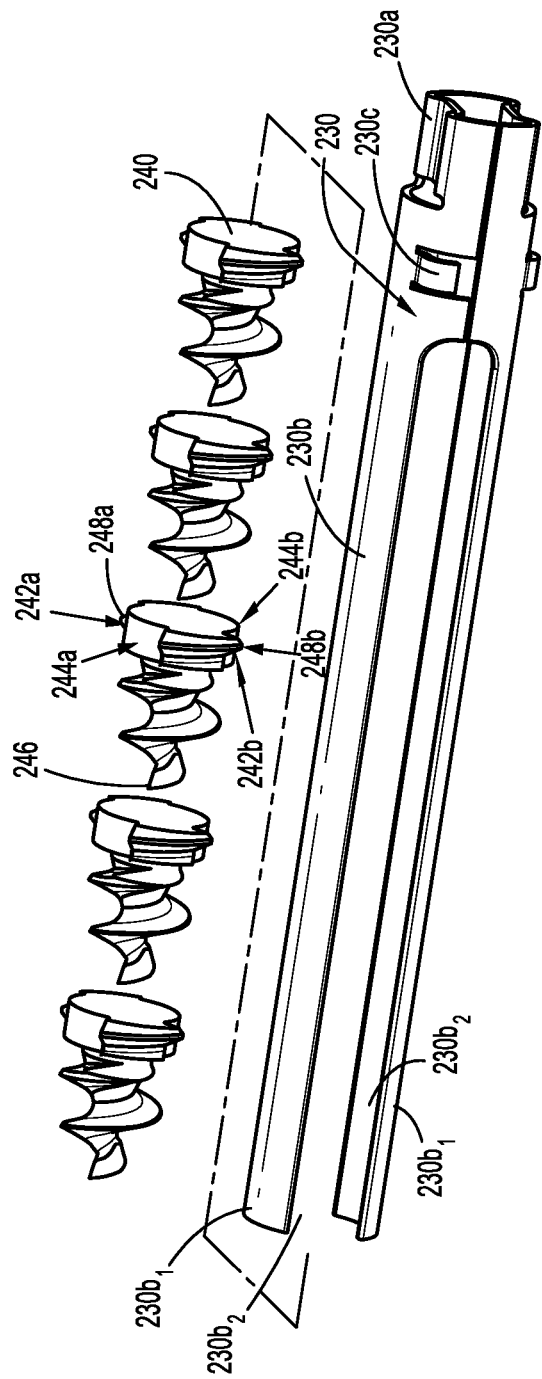
FIG. 21 is a perspective view of an inner tube of the end effector of FIG. 18, with a plurality of anchors shown separated therefrom.

As shown in FIGS. 20 and 21, the distal end portion 230b of the inner tube 230 is slotted, defining a pair of tines $230b_1$ and a pair of channels $230b_2$. The distal end portion 230b of the inner tube 230 is capable of accepting a plurality of anchors 240 within the inner tube 230. In particular, the anchors 240 are loaded into the end effector 200 such that a pair of opposing threaded sections 242a, 242b of the anchors 240 extend through respective channels $230b_2$ of the distal end portion 230b of the inner tube 230 and are slidably disposed within the groove of the coil 220, and the pair of tines $230b_1$ of the distal end portion 230b of the inner tube 230 are disposed within a pair of slotted sections 244a, 244b of the anchors 240. Each of the anchors 240 is loaded into the end effector 200 such that adjacent anchors 240 are not in contact with one another so as to not damage distal tips 246 of the anchors 240.

In an operation of the surgical tack applier 100, with the end effector 200 operatively connected to the distal support tube portion 154b of the outer support tube assembly 154 of the endoscopic assembly 150 as shown, for example, in FIGS. 13 and 14, as the inner shaft assembly 158 is rotated due to an actuation of the trigger 114, as described above, said rotation is transmitted to the inner tube 230 of the end effector 200 via the coupling member 158c of the endoscopic assembly 150. As the inner tube 230 is rotated, about its longitudinal axis, with respect to the coil 220, the pair of tines $230b_1$ of the inner tube 230 transmits the rotation to the anchors 240 and advances the anchors 240 distally owing to head threads 248a, 248b of the anchors 240 engaging with the coil 220.

A single complete and full actuation of the trigger 114 results in a firing of a single anchor 240 from the end effector 200. The surgical tacker 200 may be repeatedly fired to fire anchors 240 from the end effector 200 until the surgical procedure is complete or until the end effector 200 is spent of anchors 240. If the end effector 200 is spent of anchors 240, and if additional anchors 240 are required to complete the surgical procedure, the spent end effector 200 may be replaced with a new (e.g., loaded with anchors 240) end effector 200.

With reference again to FIGS. 2 and 5-16, in order to prepare surgical tack applier 100 for receipt of the end effector 200 or to replace a spent end effector 200 with a new end effector 200, the button 130 of the handle assembly 110 is moved from the first position to the second position, as described above, such that the trigger 114 is prevented from actuation and the slider 140 is free to move. With the button 130 in the second position, the slider 140 is moved from the first position to the second position, as also described above. As the slider 140 is moved to the second position, the second stem 140b of the slider 140 exerts a force on the proximal radial flange 158d of the inner shaft assembly 158 to urge the inner shaft assembly 158, and in turn the coupling member 158c thereof, proximally from a respective first position to a respective second position. As the coupling member 158c is moved from the first position to the second position, the ball detents 162 are free to drop or move radially inward of the outer tube 152 as the outer camming surface/relief $158c_1$ of the coupling member 158c is moved into axial registration with the ball detents 162. With the ball detents 162 free to drop or move radially inward, the end effector 200 may be fully coupled to the distal support tube portion 154b of the endoscopic assembly 150.

Once again, as mentioned above, as so configured and operable, the end effector 200 may only be removed and replaced when trigger 114 is in the fully un-actuated, home and locked position. As such, the end effector 200 cannot be removed or replaced or loaded while the trigger 114 is in a short-stroked condition (e.g., partially actuated).

With a new end effector 200 fully coupled to distal support tube portion 154b of the endoscopic assembly 150, the slider 140 is moved from the second position to the first position to secure or lock the end effector 200 to the distal support tube portion 154b of the endoscopic assembly 150. In particular, as the slider 140 is moved to the first position, the second stem 140b of the slider 140 exerts a force on the distal radial flange 158e of the inner shaft assembly 158 to urge the inner shaft assembly 158, and in turn the coupling member 158c thereof, distally from the second position to the first position. As the coupling member 158c is moved from the second position to the first position, the ball detents 162 are urged by outer the camming surface/relief $158c_1$ of the coupling member 158 to move the ball detents 162 radially outward. As the ball detents 162 move radially outward a portion of each of the ball detents 162 enters a respective aperture 210c defined in the outer tube 210 of the end effector 200 to secure the end effector 200 to the distal support tube portion 154b of the endoscopic assembly 150. With the end effector 200 coupled to the endoscopic assembly 150, the button 130 is moved from the second position to the first position, as described above, such that slider 140 is prevented from actuation and such that trigger 114 is free to move.

In order to replace a spent end effector 200 with a new end effector 200, a user actuates or slides the slider 140 to release the spent end effector 200, decouples the end effector 200 from the endoscopic assembly 150, loads or connects a new end effector 200 to the endoscopic assembly 150 by fitting the proximal end portion 230a of the inner tube 230 over the coupling member 158c of the endoscopic assembly 150, and releases the slider 140 to retain the new end effector 200 on the endoscopic assembly 150. Since the trigger 114 is in the fully un-actuated position with the loading of a new end effector 200, the timing system 123 is reset such that each full actuation of the trigger 114 results in the firing of a single anchor 240.

Figure 22:
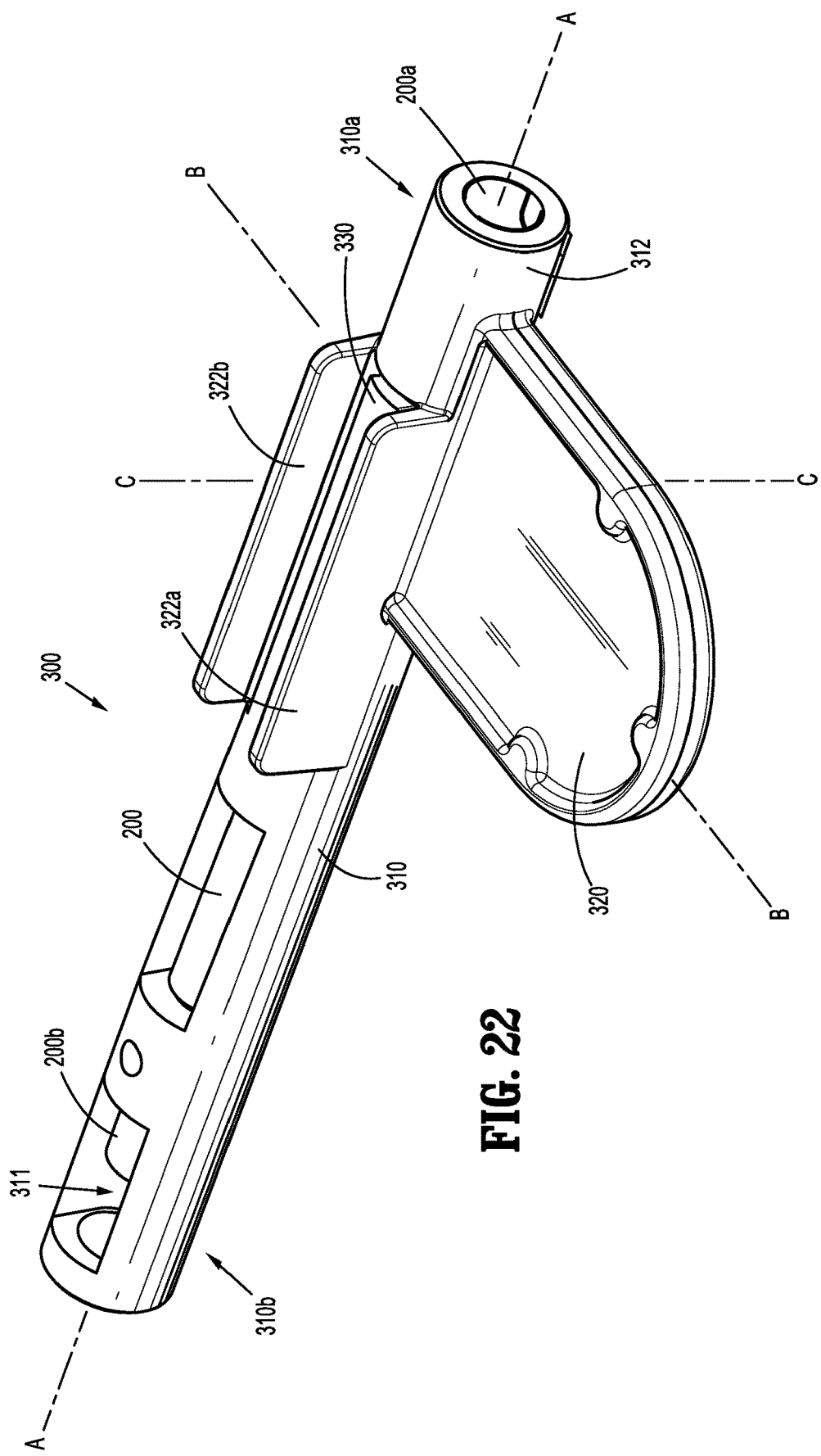
FIG. 22 is a perspective view of a shipping wedge in accordance with an embodiment of the present disclosure, installed on an end effector.

Turning now to FIG. 22, a shipping wedge 300, in accordance with an embodiment of the present disclosure, is shown disposed over an end effector 200. The shipping wedge 300 is configured and dimensioned to releasably connect to the end effector 200, to inhibit premature rotation of the inner tube 230 of the end effector 200, and to facilitate proper loading of the end effector 200 to the endoscopic assembly 150 of the surgical tack applier 100.

The shipping wedge 300 includes an elongate body 310 extending along a longitudinal axis "A". The elongate body 310 is tubular in shape and defines a lumen or channel 311 extending longitudinally therethrough. The channel 311 of the elongate body 310 has a diameter sufficient to releasably accommodate the end effector 200 therein and along. The elongate body 310 includes a proximal portion 310a defining a circumferential wall 312 configured to extend completely around a proximal end 200a of the end effector 200 and be axially aligned therewith. The elongate body 310 includes a distal portion 310b that may extend longitudinally beyond a distal end 200b of the end effector 200.

A handle or wing 320 is integrally formed with or secured to the elongate body 310. The wing 320 extends transversely from the elongate body 310 along a first transverse axis "B" that is orthogonal to the longitudinal axis "A" of the elongate body 310. The handle 320 may be utilized (e.g., gripped) by a user to load the end effector 200 onto the endoscopic assembly 150 and/or to remove the shipping wedge 300 from the end effector 200 once the end effector 200 is properly loaded onto the endoscopic assembly 150.

A pair of guard walls or rails 322a, 322b are also integrally formed with or secured to the elongated body 310. The pair of guard walls 322a, 322b extend transversely from the elongate body 310 along a second transverse axis "C" that is orthogonal to the first transverse axis "B" of the handle 320 as well as the longitudinal axis "B" of the elongate body 310. The pair of guard walls 322a, 322b is disposed in substantially parallel and spaced relation relative to each other, on opposed sides of an arm 330 disposed therebetween.

Figure 24:
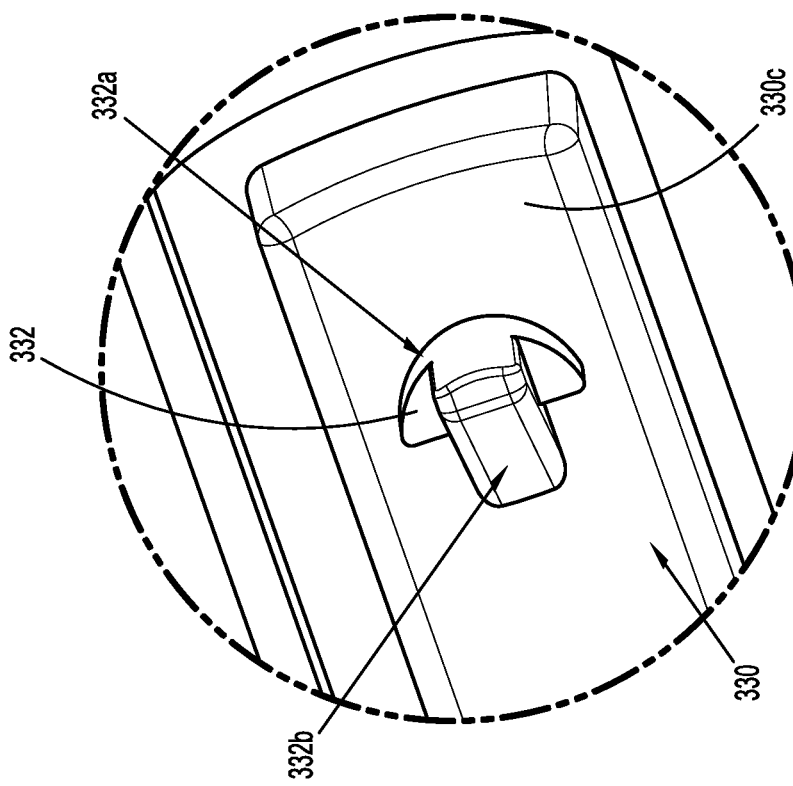
FIG. 24 is an enlarged view of a proximal portion of an arm of the shipping wedge shown in FIG. 23.
Figure 23:
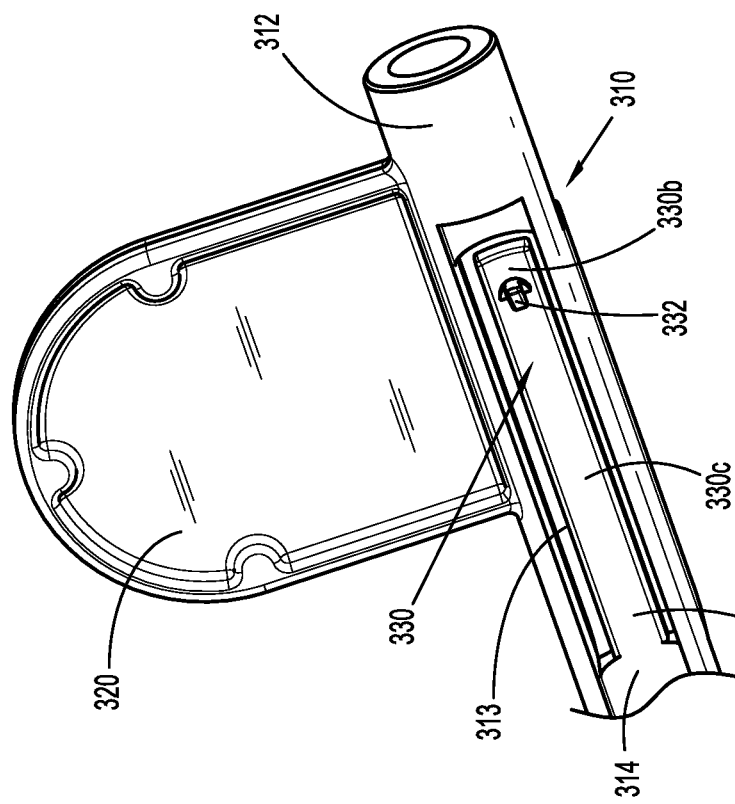
FIG. 23 is a side view of the shipping wedge of FIG. 22.

As shown in FIGS. 23 and 24, the arm 330 has a cantilever configuration including a first or distal end 330a coupled to a side wall 314 of the elongate body 310 and a second or proximal end 330b that is free to move laterally with respect to the side wall 314. The arm 330 is biased to extend within a slot 313 defined in the side wall 314. The arm 330 may be integrally formed with the side wall 314 of the elongate body 310 by cutting the slot 313 in a generally U-shape or, alternatively, the arm 330 may be secured to the side wall 314 of the elongate body 310 and positioned within the slot 313 having, for example, a rectangular shape. It is envisioned that the geometry of the slot 313 may vary and be configured to accommodate the arm 330 therein.

Figure 25:
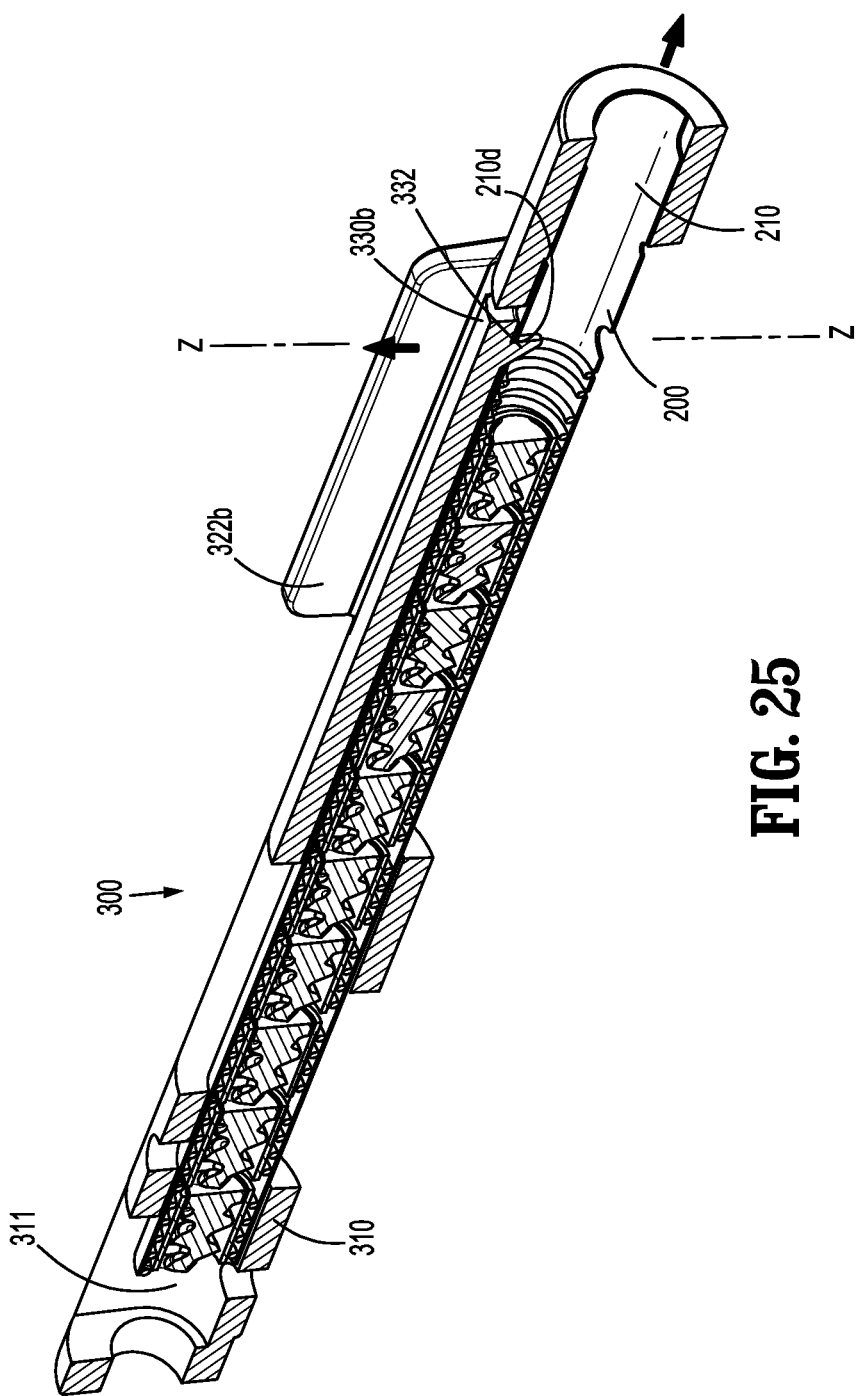
FIG. 25 is a cross-sectional view of the shipping wedge and the end effector of FIG. 22.

A projection 332 extends from an inner surface 330c of the arm 330 adjacent the proximal end 330b of the arm 330. The projection 332 includes a first surface 332a and a cam ramp 332b. As shown in FIGS. 24 and 25, the projection 332 extends into the channel 311 of the elongate body 310 along an axis that is aligned with or parallel to the second transverse axis "Z" of the pair of guard walls 322a, 322b. The first surface 332a of the projection 332 extends laterally into the channel 311 and the cam ramp 332b tapers from the first surface 332a of the projection 332 distally towards the inner surface 330c of the arm 330. The projection 332 is configured and dimensioned for insertion into an aperture 210d (see also, FIG. 18) defined in the outer tube 210 of the end effector 200.

When the shipping wedge 300 is attached to the end effector 200, the projection 332 extends in close proximity to or in contact with the proximal end portion 230a (see e.g., FIG. 19) of the inner tube 230 of the end effector 200. By extending this amount, the projection 332 inhibits rotation of the inner tube 230 relative to the outer tube 210 by blocking or contacting the proximal end portion 230a of the inner tube 230 if the inner tube 230 experiences any rotation relative to the outer tube 210. The first surface 332a of the projection 332 further ensures simultaneous advancement of the end effector 200 with the shipping wedge 300 by inhibiting advancement of the shipping wedge 300 relative to the end effector 200 during assembly of the end effector 200 onto the endoscopic assembly 150 of the surgical tack applier 100. The cam ramp 332b of the projection 332 enables the arm 330 to be deflected laterally outward and away from the end effector 200 upon proper loading of the end effector 200 to the endoscopic assembly 150 for removal of the shipping wedge 300 from the end effector 200, as described in further detail below.

The end effector 200, with the shipping wedge 300 installed thereon as shown, for example in FIG. 22, is loaded onto the endoscopic assembly 150 of the surgical tack applier 100 (see e.g., FIG. 1) by first preparing the surgical tack applier 100 for receipt of the end effector 200 by moving the slider 140 from the first position to the second position, as described above, to urge the inner shaft assembly 158, and thus the coupling member 158c, proximally from the first position to the second position as shown, for example, in FIGS. 15 and 16. As the coupling member 158c is moved from the first position to the second position, the ball detents 162 drop or move radially inward of the outer tube 152 as the outer camming surface/relief $158c_1$ of the coupling member 158c is moved into axial registration with the ball detents 162 so that the end effector 200 may be fully coupled to the distal support tube portion 154b of the endoscopic assembly 150.

The end effector 200 with attached shipping wedge 300 is then advanced over the endoscopic assembly 150 such that the distal support tube portion 154b of the endoscopic assembly 150 is received within the outer tube 210 of the end effector 200 with the key 154d (FIG. 18) of the outer support tube assembly 154 positioned within the proximal key slot 210b of the outer tube 210 of the end effector 200. With the end effector 200 fully coupled to distal support tube portion 154b of the endoscopic assembly 150, the slider 140 is moved from the second position to the first position, as described above, to secure or lock the end effector 200 to the distal support tube portion 154b of the endoscopic assembly 150. In particular, as the slider 140 is moved to the first position, the inner shaft assembly 158, and in turn the coupling member 158c thereof, is moved distally from the second position to the first position. As the coupling member 158c is moved from the second position to the first position, the ball detents 162 are urged by the outer camming surface/relief $158c_1$ of the coupling member 158 to move the ball detents 162 radially outward as shown, for example, in FIGS. 13 and 14. As the ball detents 162 move radially outward a portion of each of the ball detents 162 enters the respective aperture 210c defined in the outer tube 210 of the end effector 200 to secure the end effector 200 to the distal support tube portion 154b of the endoscopic assembly 150.

The shipping wedge 300 fully encompasses the end effector 200 to prevent a user from forcing the end effector 200 onto the surgical tack applier 100 during installation thereof. The circumferential wall 312 of the elongate body 310 of the shipping wedge 300 prevents or minimizes deformation of the outer tube 210 of the end effector 200 during the installation onto the endoscopic assembly 150 (e.g., by preventing a user's ability to force the end effector 200 onto the endoscopic assembly 150 which may result in premature separate of the end effector 200 from the surgical tack applier 100). Under the retention force of a properly loaded end effector 200, the arm 330 of the shipping wedge 300 will flex or be deflected away from the end effector 200 via the cam ramp 332b of the protrusion 332 so that the shipping wedge 300 can be removed from the end effector 200 by sliding the shipping wedge 300 linearly along and away from the end effector 200.

The shipping wedge 300 ensures proper loading of the end effector 200 onto the endoscopic assembly 150 of the surgical tack applier 100 as the shipping wedge 300 will only separate from the end effector 200 when properly loaded onto the endoscopic assembly 150. The shipping wedge 300 will not separate from the end effector 200 until a force is reach that is less than a force it takes to remove a properly loaded end effector 200 from the endoscopic assembly 150 but greater than a force it takes to remove the end effector 200 from the endoscopic assembly 150 when the ball detents 162 are not fully/properly engaged. This configuration eliminates a false position that the end effector 200 is properly engaged with the endoscopic assembly 150 by, for example, preventing a user from forcing the end effector 200 onto the endoscopic assembly 150 improperly and/or preventing the shipping wedge 300 from being removed from the end effector 200 if the ball detents 162 are not properly and fully engaged with the end effector 200.

With reference now to FIG. 26, a shipping wedge 400, in accordance with another embodiment of the present disclosure, is shown. The shipping wedge 400 is configured and dimensioned to releasably connect to an end effector 200, as shown in FIG. 27, and to facilitate loading of the end effector 200 to the endoscopic assembly 150 of the surgical tack applier 100 while inhibiting premature actuation of the end effector 200.

As shown in FIGS. 26 and 27, the shipping wedge 400 includes an elongate body 410 extending along a longitudinal axis "Y". The elongate body 410 includes a proximal portion 410a and a distal portion 410b, and defines a channel 411 extending longitudinally therethrough that is configured and dimensioned to receive and releasably retain the end effector 200 therein. A distal portion 411b of the channel 411 defined in the distal portion 410b of the elongate body 410 is substantially tubular in shape and extends completely around a distal portion 200b of the end effector 200 to securely retain the end effector 200 therein. The distal portion 410b of the elongate body 410 may include side cut outs 412 to facilitate the formation of the channel 411 therein, or the distal portion 410b of the elongate body 410 may be solid with the channel 411 formed by molding the elongate body 410 about a core pin. The distal portion 410b of the elongate body 410 may extend longitudinally beyond the distal portion 200b of the end effector 200 and have a closed end 410c.

The proximal portion 410a of the elongate body 410 includes first and second arms 414, 416 that extend proximally from the distal portion 410b. The first arm 414 is biased to extend along an axis that is disposed at an angle with respect to the longitudinal axis "Y", and the second arm 416 is biased to extend along an axis that is substantially parallel to the longitudinal axis "Y". The first arm 414 includes a pair of fingers 414a, 414b extending towards the second arm 416. The pair of fingers 414a, 414b are disposed in parallel and spaced relation relative to each other and define a slot 414c therebetween that is coincident with the channel 411 of the elongate body 410 and dimensioned to receive the end effector 200 therein. The second arm 416 includes a locking tab 418 secured thereto that extends towards the first arm 414 and into the slot 414c defined between the pair of fingers 414a, 414b. The locking tab 418 extends along a transverse axis "Z" that is orthogonal to the longitudinal axis "Y". The locking tab 418 is formed from a rigid material to prevent or minimize deflection away from the transverse axis "Z".

The locking tab 418 is configured for positioning within the end effector 200 as shown in FIGS. 27 and 28. The locking tab 418 extends through the aperture 210d defined in the outer tube 210 of the end effector 200 and extends in close proximity to or in contact with the proximal end portion 230a of the inner tube 230 of the end effector 200. By extending this amount, the locking tab 418 inhibits rotation of the inner tube 230 relative to the outer tube 210 by blocking or contacting the proximal end portion 230a of the inner tube 230 if the inner tube 230 experiences any rotation relative to the outer tube 210.

The first and second arms 414, 416 are flexible so that the first arm 414 may be pressed towards the second arm 416, as shown in FIG. 29. Upon pressing the first arm 414 toward the second arm 416, the first arm 414 is displaced and moves to a deflected position such that the first arm 414 extends along an axis substantially parallel to the longitudinal axis "Y" of the elongate body 410. The pair of fingers 414a, 414b of the first arm 414 contacts and acts on the second arm 416 by pushing the second arm 416 away from the end effector 200 such that the second arm 416 is displaced and moved to a deflected position that extends along an axis disposed at an angle with respect to the longitudinal axis "Y" of the elongate body 410. Movement of the second arm 416 to the deflected position causes the locking tab 418 to disengage from the end effector 200.

As shown in FIGS. 27 and 28, the end effector 200, with the shipping wedge 400 installed thereon, is loaded onto the endoscopic assembly 150 of the surgical tack applier 100 without requiring the slider 140 (see e.g., FIG. 11) of the surgical tack applier 100 to be actuated (e.g., moved from the first position to the second position). The end effector 200, with the attached shipping wedge 400, is advanced over the endoscopic assembly 150 such that the distal tube portion 154b of the endoscopic assembly 150 is received within the outer tube 210 of the end effector 200. As shown in FIG. 30, as the end effector 200 is advanced towards the endoscopic assembly 150, the locking tab 418 of the shipping wedge 400 contacts the coupling member 158c of the inner shaft assembly 158 of the endoscopic assembly 150 and moves the coupling member 158c and thus, the inner shaft assembly 158 proximally from the first position to the second position. As the coupling member 158c is moved from the first position to the second position, the ball detents 162 drop or move radially inward of the outer tube 152 thereby allowing the end effector 200 to be installed thereon. As the inner shaft assembly 158 is moved to the second position, the slider 140 is also moved from the first position to the second position.

Once the key 154d (FIG. 18) of the outer support tube 154 is positioned within the proximal key slot 210b of the outer tube 210 of the end effector 200 during insertion of the end effector 200 onto the endoscopic assembly 150, the first arm 414 is pressed towards the end effector 200 which, in turn, moves the second arm 416 away from the end effector 200 as shown in FIG. 31. Movement of the second arm 416 away from the end effector 200 causes the locking tab 418 to disengage from the end effector 200. With the force of the locking tab 418 removed, the inner shaft assembly 158 and thus, the coupling member 158c, of the endoscopic assembly 150 moves distally from the second position to the first position. As the coupling member 158c is moved from the second position to the first position, the ball detents 162 are urged by the outer camming surface/relief $158c_1$ of the coupling member 158c to move the ball detents 162 radially outward such that a portion of each of the ball detents 162 enters the respective aperture 210c defined in the outer tube 210 of the end effector 200 to secure the end effector 200 to the distal support tube portion 154b of the endoscopic assembly 150. Accordingly, as the inner shaft assembly 158 is moved back to the first position, the slider 140, which may be biased in the first position as described above, is also moved back to the first position. With the end effector 200 loaded onto the endoscopic assembly 150, the shipping wedge 400 is removed from the end effector 200 by sliding the shipping wedge 400 linearly along and distally away from the end effector 200.

The shipping wedge 400 allows for the installation load to be distributed around the hand of the user and to the distal end 200b of the end effector 200. The locking tab 418 prevents the inner shaft assembly 158 from connecting to the end effector 200 until displaced thereby preventing the inner tube 230 of the end effector 200 from spinning as well as the inner shaft assembly 158 of the endoscopic assembly 150 from spinning until the trigger 114 is pulled. Additionally, the locking tab 418 displaces the inner shaft assembly 158 linearly to release the ball detents 162 thereby allowing the end effector 200 to be installed onto the endoscopic assembly 150 without having to move the slider 140 manually. Accordingly, the slider 140 is actuated by a user only to remove an end effector 200 from the endoscopic assembly 150, as described above. As the slider 140 travels in an opposite direction as the removal of the end effector 200, it is more ergonomic to use the slider 140 for removal of the end effector 200 than for installation.

Figure 32:
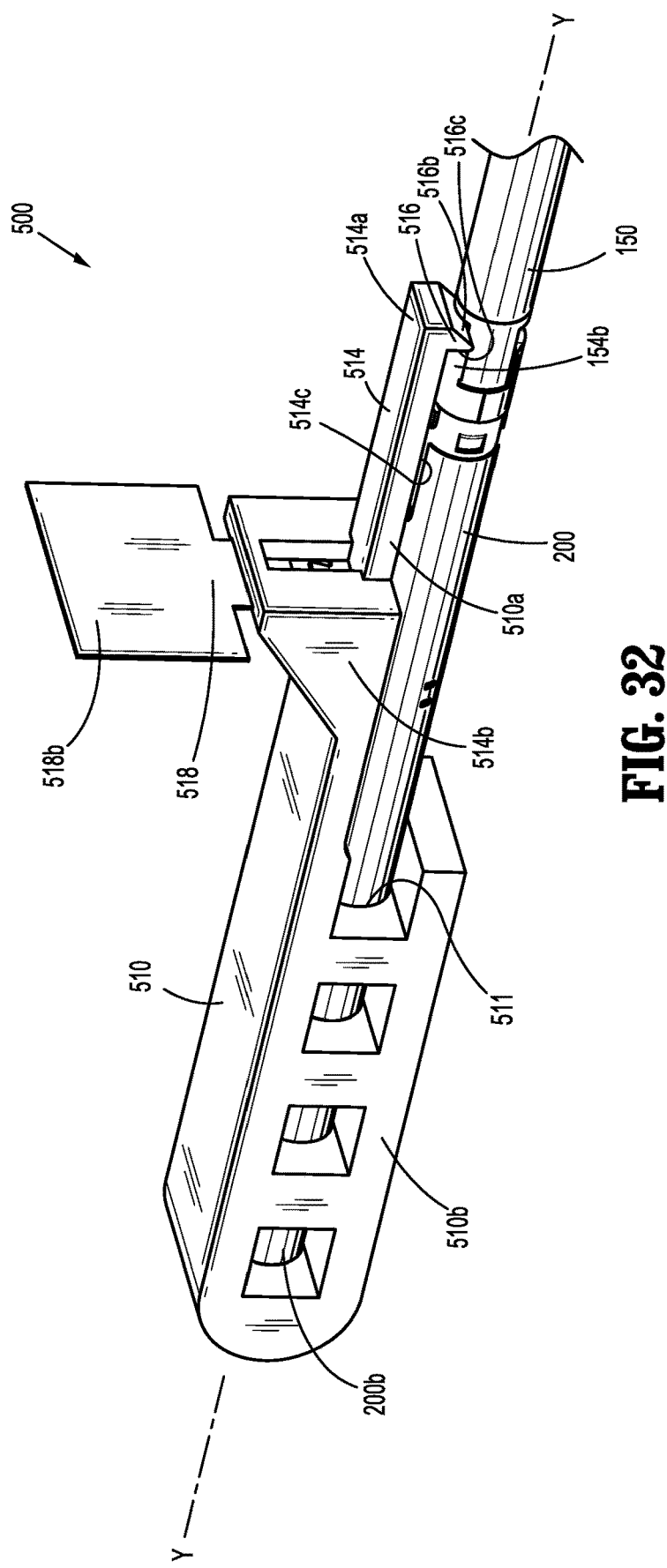
FIG. 32 is a rear, perspective view of a shipping wedge in accordance with yet another embodiment of the present disclosure, installed on an end effector.

Turning now to FIG. 32, a shipping wedge 500 in accordance with another embodiment of the present disclosure, is shown releasably disposed over an end effector 200. The shipping wedge 500 is substantially similar to the shipping wedge 400 and will be described with respect to the differences therebetween.

Figure 33:
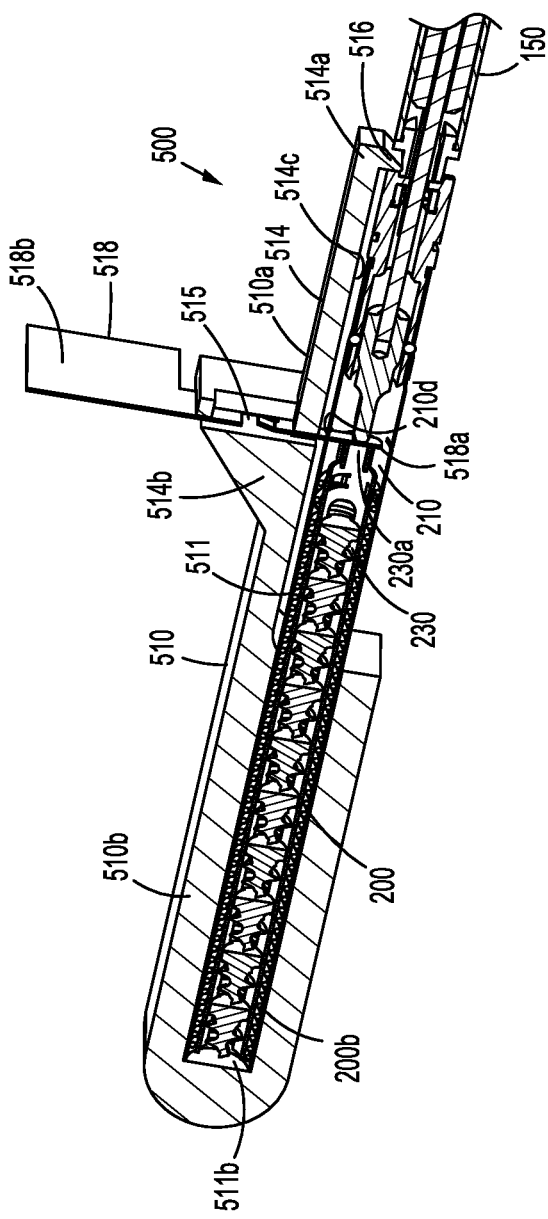
FIG. 33 is a cross-sectional view of the shipping wedge and the end effector of FIG. 32, illustrating the shipping wedge in a locked configuration during installation on an endoscopic assembly of the endoscopic surgical device of FIG. 1.

As shown in FIGS. 32 and 33, the shipping wedge 500 includes an elongated body 510 extending along a longitudinal axis "Y". The elongate body 510 includes a proximal portion 510a and a distal portion 510b, and defines a channel 511 extending longitudinally therethrough that is configured and dimensioned to receive and releasably retain the end effector 200 therein. The distal portion 510b of the elongate body 510 defines a distal portion 511b of the channel 511 that is substantially tubular in shape and extends completely around the distal portion 200b of the end effector 200.

The proximal portion 510a of the elongate body 510 includes at least one arm 514 extending proximally from the distal portion 510b along an axis substantially parallel to the longitudinal axis "Y" of the elongate body 510. The arm 514 includes a proximal portion 514a including a protuberance or latch 516 extending from an inner surface 514c of the arm 514. The latch 516 includes a first surface 516a and a cam ramp 516b. The latch 516 extends into the channel 511 of the elongate body 510 with the first surface 516a extending laterally into the channel 511 and the cam ramp 516b tapering from the first surface 516a proximally towards the inner surface 514c of the arm 514. The latch 516 is configured and dimensioned to releasably engage a proximal end of the distal tube portion 154b of the endoscopic assembly 150.

The arm 514 includes a distal portion 514b including a slit 515 defined therethrough. A locking tab 518 is slidably disposed within the slit 515. The locking tab 518 includes a first end 518a positionable within the channel 511 of the elongate body 510 and a second end 518b positioned radially outward of the arm 514. The second end 518b defines a pull tab that is engageable by a user to move the locking tab 518 from a first position in which the first end 518a of the locking tab 518 is positioned within the channel 511 of the elongate body 510, as shown in FIG. 33, and a second position in which the first end 518a of the locking tab 518 is moved into the slit 515 defined in the arm 514, as shown in FIG. 34.

The locking tab 518 is configured for positioning within the end effector 200 as shown in FIGS. 32 and 33. The locking tab 518 extends through the aperture 210d defined in the outer tube 210 of the end effector 200 and extends in close proximity to or in contact with the proximal end portion 230a of the inner tube 230 of the end effector 200. The end effector 200, with the shipping wedge 500 installed thereon, is loaded onto the endoscopic assembly 150 in a similar manner as discussed above with regard to the shipping wedge 400, except that the end effector 200 is advanced over the endoscopic assembly 150 until the latch 516 of the arm 514 of the shipping wedge 500 engages the endoscopic assembly 150.

Figure 34:
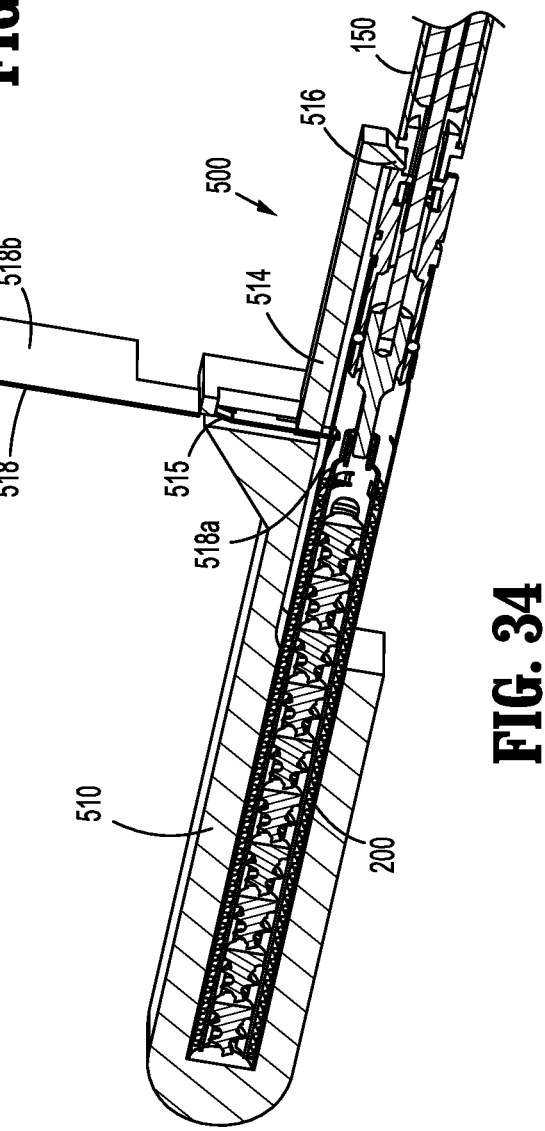
FIG. 34 is a cross-sectional view of the shipping wedge and the end effector of FIG. 32, illustrating the shipping wedge in an unlocked configuration during installation on an endoscopic assembly of the endoscopic surgical device of FIG. 1.

Once the end effector 200 is fully inserted onto the endoscopic assembly 150, the second end 518b of the locking tab 518 is pulled by a user to remove the first end 518a of the locking tab 518 from within the end effector 200, as shown in FIG. 34, to secure the end effector 200 to the endoscopic assembly 150, as described above with regard to the shipping wedge 400. Pulling on the locking tab 518 causes the arm 514 of the shipping wedge 500 to flex or be deflected laterally away from the end effector 200 which releases the latch 516 so that the shipping wedge 500 can be removed from the end effector 200 by sliding the shipping wedge 500 linearly along and distally away from the end effector 200.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A shipping wedge comprising:
    an elongate body extending along a longitudinal axis and defining a channel therethrough, the elongate body including a side wall including a slot formed therein; and
    an arm integrally formed with the side wall and disposed within the slot of the elongate body, the arm including a first end coupled to the side wall and a second end that is movable laterally with respect to the side wall, the first end of the arm is biased to extend within the slot of the side wall and the second end of the arm is deflectable out of the slot.

2. The shipping wedge according to claim 1, further comprising a handle extending transversely from the elongate body.

3. The shipping wedge according to claim 1, wherein the arm includes a projection extending from an inner surface of the arm.

4. The shipping wedge according to claim 3, wherein the projection of the arm includes a first surface extending laterally into the channel of the elongate body.

5. The shipping wedge according to claim 3, wherein the projection of the arm includes a cam ramp tapering distally towards the inner surface of the arm.

6. The shipping wedge according to claim 1, further comprising a pair of guide walls extending transversely from the elongate body in substantially parallel and spaced relation relative to each other on opposed sides of the slot of the side wall.

7. The shipping wedge according to claim 1, wherein the elongate body includes a proximal portion defining a circumferential wall extending completely around the channel defined in the elongate body.

8. The shipping wedge according to claim 1, wherein the elongate body is tubular.

9. The shipping wedge according to claim 6, wherein the pair of guide walls extend outwardly from the elongate body and away from the channel defined therein.

10. An assembly comprising:
    the shipping wedge of claim 1; and
    an end effector including an outer tube having proximal and distal ends and an inner tube disposed within the outer tube, the inner tube rotatable relative to the outer tube,
    wherein the shipping wedge is removably installed on the end effector with the end effector received within the channel of the shipping wedge such that a proximal portion of the elongate body is axially aligned with the proximal end of the end effector and a distal portion of the elongate body extends longitudinally beyond the distal end of the end effector.

11. The assembly according to claim 10, wherein the outer tube of the end effector defines an aperture therethrough and the arm of the shipping wedge includes a projection extending from an inner surface thereof and wherein, the projection extends through the aperture of the outer tube and into contact with a proximal end portion of the inner tube to inhibit rotation of the inner tube relative to the outer tube.

12. A shipping wedge comprising:
    an elongate body extending along a longitudinal axis and defining a channel therethrough, the elongate body including a side wall having a slot formed therein and a proximal portion defining a circumferential wall extending completely around the channel; and
    an arm integrally formed with the side wall and disposed within the slot of the elongate body, the arm including a first end coupled to the side wall and a second end that is movable laterally with respect to the side wall.

13. The shipping wedge according to claim 12, further comprising a handle extending transversely from the elongate body.

14. The shipping wedge according to claim 12, wherein the arm includes a projection extending from an inner surface of the arm.

15. The shipping wedge according to claim 12, further comprising a pair of guide walls extending transversely from the elongate body in substantially parallel and spaced relation relative to each other on opposed sides of the slot of the side wall.

16. The shipping wedge according to claim 12, wherein the elongate body is tubular.

17. A shipping wedge comprising:
an elongate body extending along a longitudinal axis and defining a channel therethrough, the elongate body including a side wall including a slot formed therein and a pair of guide walls extending transversely outwardly from the elongate body and away from the channel in substantially parallel and spaced relation relative to each other on opposed sides of the slot; and
an arm integrally formed with the side wall and disposed within the slot of the elongate body, the arm including a first end coupled to the side wall and a second end that is movable laterally with respect to the side wall.

18. The shipping wedge according to claim 17, further comprising a handle extending transversely from the elongate body.

19. The shipping wedge according to claim 17, wherein the arm includes a projection extending from an inner surface of the arm.

20. The shipping wedge according to claim 17, wherein the elongate body is tubular.

* * * * *